(12) United States Patent
Sakamoto et al.

(10) Patent No.: US 11,767,545 B2
(45) Date of Patent: Sep. 26, 2023

(54) MICROORGANISM AND METHOD FOR PRODUCING TRIACYLGLYCEROL

(71) Applicants: HIROSHIMA UNIVERSITY, Hiroshima (JP); TOKYO INSTITUTE OF TECHNOLOGY, Tokyo (JP); MAZDA MOTOR CORPORATION, Hiroshima (JP)

(72) Inventors: Atsushi Sakamoto, Higashihiroshima (JP); Kumiko Okazaki, Higashihiroshima (JP); Takashi Yamamoto, Higashihiroshima (JP); Hiroyuki Ohta, Tokyo (JP); Koichi Hori, Tokyo (JP); Shinsuke Shimizu, Tokyo (JP); Akihide Takami, Hiroshima (JP); Seiji Nomura, Hiroshima (JP); Fumihiko Saito, Hiroshima (JP)

(73) Assignees: HIROSHIMA UNIVERSITY, Hiroshima (JP); TOKYO INSTITUTE OF TECHNOLOGY, Tokyo (JP); MAZDA MOTOR CORPORATION, Hiroshima (JP)

(*) Notice: Subject to any disclaimer, the term of this patent is extended or adjusted under 35 U.S.C. 154(b) by 0 days.

(21) Appl. No.: 17/272,862

(22) PCT Filed: Sep. 6, 2019

(86) PCT No.: PCT/JP2019/035244
§ 371 (c)(1),
(2) Date: Mar. 2, 2021

(87) PCT Pub. No.: WO2020/050412
PCT Pub. Date: Mar. 12, 2020

(65) Prior Publication Data
US 2021/0317482 A1    Oct. 14, 2021

(30) Foreign Application Priority Data
Sep. 7, 2018   (JP) .............................. 2018-168235

(51) Int. Cl.
*C12P 7/6463* (2022.01)
*C12N 1/12* (2006.01)
*C12R 1/89* (2006.01)

(52) U.S. Cl.
CPC .............. *C12P 7/6463* (2013.01); *C12N 1/12* (2013.01); *C12R 2001/89* (2021.05)

(58) Field of Classification Search
CPC ...... C12P 7/6463; C12N 1/12; C12R 2001/89
See application file for complete search history.

(56) References Cited

U.S. PATENT DOCUMENTS

2017/0073711 A1   3/2017   Iwai et al.

FOREIGN PATENT DOCUMENTS

| JP | 5988212 B2 | 9/2016 | |
|----|----|----|----|
| WO | 2015/137449 A1 | 9/2015 | |
| WO | WO-2015137449 A1 * | 9/2015 | ................ C12P 7/64 |

OTHER PUBLICATIONS

Kumiko Okazaki et a l."2aG09: Functional Analysis of SPX-like Gene in Nannochloropsis" Proceedings of the 82nd nnual Meeting of the Botanical Society of Japan, Hiroshima 2018, p. 188, The Botanical Society of Japan. As cited in IDS (Year: 2018).*
EWM26150.1 (NCBI Reference Sequence, priority to Feb. 14, 2014, 2 pages) (Year: 2014).*
Iwai, Masako, WO-2015137449-A1, machine translation (Year: 2015).*
Zhang, S. F., Yuan, C. J., Chen, Y., Chen, X. H., Li, D. X., Liu, J. L., ... & Wang, D. Z. (2016). Comparative transcriptomic analysis reveals novel insights into the adaptive response of Skeletonema costatum to changing ambient phosphorus. Frontiers in microbiology, 7, 1476 (Year: 2016).*
Setyaningsi, E. P., Nurhidayati, T., Pratiwi, S., Nurhatika, S., , . . . & Tsai, M. J. (Jun. 2018). Microalgae Growth and Morphology of Skeletonema costatum On Physiological Stress Nutrient Silicon (Si). In Journal of Physics: Conference Series (vol. 1028, No. 1, p. 01204 (Year: 2018).*
Daboussi F. Leduc S. Marechal A. Dubois G. Guyot V. Perez-Michaut C. et al. . ( 2014 ) Genome engineering empowers the diatom Phaeodactylum tricornutum for biotechnology . Nat. Commun.5 : 3831 . (Year: 2014).*
Corteggiani Carpinelli E., Telatin A., Vitulo N., Forcato C., D'Angelo M., Schiavon R., Vezzi A., Giacometti G.M., Morosinotto T., Valle G.; Chromosome Scale Genome Assembly and Transcriptome Profiling of Nannochloropsis gaditana in Nitrogen Depletion (Year: 2014).*
Molla, K. A., & Yang, Y. (2020). Predicting CRISPR/Cas9-induced mutations for precise genome editing. Trends in biotechnology, 38(2), 136-141. (Year: 2020).*
International Search Report issued in PCT/JP2019/035244; dated Nov. 12, 2019.
Na Liu et al. "Evolution of the SPX Gene Family in Plants and Its Role in the Response Mechanism to Phosphorus Stress" Open Biology, Jan. 3, 2018, pp. 1-10, vol. 8: 170231.
Alice Muhlroth et al. "Mechanisms of Phosphorus Acquisition and Lipid Class Remodeling Under P Limitation in a Marine Microalga" Plant Physiology, Oct. 19, 2017, pp. 1543-1559, vol. 175.
Kumiko Okazaki et al. "2aG09: Functional Analysis of SPX-like Gene in Nannochloropsis" Proceedings of the 82nd Annual Meeting of the Botanical Society of Japan, Hiroshima 2018, p. 188, The Botanical Society of Japan.
Masako Iwai et al. "Manipulation of oil synthesis in Nannochloropsis strain NIES-2145 with a phosphorus starvation-inducible promoter from Chlamydomonas reinhardtii" frontiers in Microbiology, Sep. 7, 2015, pp. 1-15, vol. 6, Article 912.

(Continued)

*Primary Examiner* — Louise W Humphrey
*Assistant Examiner* — Trevor Kane
(74) *Attorney, Agent, or Firm* — Studebaker & Brackett PC

(57) ABSTRACT

A microorganism having at least one SPX gene encoding SPX protein responsive to phosphorus deficiency, and characterized in that a function of the SPX protein is decreased or lost by introducing gene mutation into the SPX gene.

6 Claims, 11 Drawing Sheets

Specification includes a Sequence Listing.

(56) References Cited

OTHER PUBLICATIONS

Masako Iwai et al. "Modification of Nannochloropsis Oil Synthesis Using Phosphorus-deficient Responsive Promoter, A Phosphorus Starvation-inducible Promoter is Effective in Manipulating TAG Synthesis in Nannochloropsis" Industrial Prospects for Oils/Components Produced by Microalgae, Bio Industry, 2016, pp. 5-9, vol. 33, No. 7.

W7THB6_9STR, Full=Vacuolar transporter chaperone 4 [online], 2017. <https://www.uniprot.org/uniprot/W7THB6.txt?version=11> searched on Oct. 30, 2019.

Rebekka Wild et al.; "Control of eukaryotic phosphate homeostasis by inositol polyphosphate sensor domains" Science; vol. 352; No. 6288; May 20, 2016; pp. 986-990; XP055903125.

* cited by examiner

1 WILD-TYPE
2 *spx2* KNOCKOUT STRAIN

1 WILD-TYPE
2 *spx2* KNOCKOUT STRAIN ns the electronic sequence listing (Name:
sequence-listing.txt; Date of Creation: May 9, 2022; and
Size: 36,157 bytes) is herein incorporated by reference in its
entirety.

SEQUENCE LISTING

```
<160> NUMBER OF SEQ ID NOS: 15

<210> SEQ ID NO 1
<211> LENGTH: 363
<212> TYPE: PRT
<213> ORGANISM: Nannochloropsis sp.

<400> SEQUENCE: 1

Met Lys Phe Gly Lys Gln Leu Ala Lys Val Val Ala Leu Ser Asp Pro
1               5                   10                  15

Glu Trp Ala Pro Phe Trp Val Ser Tyr Lys Ala Leu Lys Lys Arg Val
            20                  25                  30

Lys Glu Leu Thr Asp Ser Pro Pro Gly Thr Gln Pro Arg Asp Ala
        35                  40                  45

Gly Thr Val Ala His Gly His His Ser Ala Pro Ala Thr Asn Thr Glu
    50                  55                  60

Pro Asn Pro Lys Glu Leu Ala Gln Ser Val Gly Glu Val Ala Phe Phe
65                  70                  75                  80

Arg Thr Leu Arg Ala Glu Val Ala Lys Ala Ser Glu Phe Phe Leu Gly
```

```
            85                  90                  95
Met Glu Gln Gln Met Gly Ala Arg Arg Arg Ile Lys Met Gly Leu
                100                 105                 110

Gln Tyr Met Lys Gln Pro Thr Thr Val Leu Glu Asp Ala Trp Met
                115                 120                 125

Lys Met Arg Arg Ala Cys Ile Ser Leu Tyr Lys Asp Leu Leu Leu
                130                 135                 140

Glu Asn Phe Ala Val Met Asn Tyr Cys Ala Cys Ser Lys Ala Leu Lys
145                 150                 155                 160

Lys His Asp Lys Thr Val Val Leu Asp Thr Arg Ala Arg Phe Met Arg
                165                 170                 175

Asn Val Val Asn Gln Gln Pro Phe Thr His Tyr Pro Arg Leu Leu Glu
                180                 185                 190

Met Leu Gln Glu Met Glu Glu Thr Phe Lys Glu Ile Asp Ala Ser Gln
                195                 200                 205

Gly Asp Thr Ala Arg Pro Leu Glu Asp Glu Glu Arg Leu Phe Leu Glu
210                 215                 220

Ala Ile Arg Gly Leu Asn Gln Glu Ala Ser Ser Met Gln Arg Glu Glu
225                 230                 235                 240

Lys Ala Asp Leu Gly His Thr Ser Ser Thr Ser Asp Gln Glu His Ser
                245                 250                 255

Ala Asp Asp Gln Pro Ala Ala Ser Asp Ala Ala Thr Gly Arg Asn
                260                 265                 270

Ala Ala Thr Pro Ile Asn Ala Thr Thr Asn Asn Asp Thr Arg Gly Ala
                275                 280                 285

Ala Ser Glu Ser Val Ser Gln Ser Lys Arg Leu Lys Thr Gln Lys Pro
                290                 295                 300

Ala Ala Ala Ile Val Pro Glu Trp Arg Gly Thr Gly Asp Gly Asp
305                 310                 315                 320

Gly Ala Gly Leu Gly Ala Gly Ala Gly Glu His Ala Lys Gly Gly
                325                 330                 335

Lys Leu Lys Glu Ala Arg Pro Ala Glu Glu Val Glu Ala Glu Pro Ala
                340                 345                 350

Gly Gly Glu Ser Ala Gly Lys Arg Arg Val
                355                 360

<210> SEQ ID NO 2
<211> LENGTH: 761
<212> TYPE: PRT
<213> ORGANISM: Nannochloropsis sp.

<400> SEQUENCE: 2

Met Lys Phe Gly Leu Tyr Leu Arg Glu Asn Val Glu Glu Trp Lys
1               5                   10                  15

Gln Tyr Tyr Leu Gln Tyr Asp Lys Leu Lys Arg Met Ile Arg Ile Leu
                20                  25                  30

Ala Glu Val Glu Ser Lys Ala Met Ala Pro Glu Pro Thr Leu Thr Gly
                35                  40                  45

Lys Val Gly Phe Ser Leu Thr Val Pro Pro Thr Asn Ala Ala Ala
50                  55                  60

Gln Pro Leu Gly Arg Ala Gly Lys Gly Met Gly Val Met Asp Gly
65                  70                  75                  80

Asp Ser Asp Asp Glu Asp Ser Ser Gly Gly Asp Glu Ala Asp Ala Ala
                85                  90                  95
```

```
Pro Val Thr His Glu Leu Phe Phe Asp Leu Leu Glu Lys Glu Ile Gln
            100                 105                 110

Lys Val His Asn Phe Thr Asp Arg Lys Val Thr Glu Ile Arg Ala Lys
        115                 120                 125

Leu Arg Asp Val Gly Lys Arg Leu Lys Ile Gly Thr Ile Glu Val Val
    130                 135                 140

Pro Gly Gly Gln Pro Leu Glu Ile Gly Asp Ala Val Arg Lys Glu Val
145                 150                 155                 160

Asp Glu Val Gly Glu Gln Phe Leu Arg Leu Glu Lys Tyr Val Asn Leu
                165                 170                 175

Asn Tyr Thr Gly Phe His Lys Ile Leu Lys Lys His Asp Arg Trp Leu
            180                 185                 190

Thr Asn Pro Cys Arg Thr Phe Tyr Leu Gln Arg Leu Gln Asn His Asn
        195                 200                 205

Trp Thr Gln Gly Asp Tyr Ser Asp Val Val Thr Met Ser Gln Ile
    210                 215                 220

Trp Ser Ala Leu Arg Gly Asp Val Ala Pro Glu Gly Thr Ala Thr Glu
225                 230                 235                 240

Ser Gln Glu Phe Val Arg Ser Thr Thr Lys Tyr Trp Ile Gln Asp Glu
                245                 250                 255

Asp Ile Ser Gln Leu Lys Trp Phe Val Leu Gln His Leu Pro Val Leu
            260                 265                 270

Leu Gln Glu Ser Met Gly Thr Lys Ser Asp Ser Gln Leu Val Asn Ser
        275                 280                 285

Val Tyr Leu Asp Asn Ala Thr Leu Glu Leu Tyr Lys Gly Arg Leu Asp
    290                 295                 300

Lys Thr Pro Gly Ala Ile Ala Val Arg Phe Arg Trp Tyr Gly Ser Gly
305                 310                 315                 320

Thr Pro Glu Leu Val Phe Val Glu Arg Lys Thr His Arg Glu Ala Trp
                325                 330                 335

Thr Ala Glu Met Ser Val Lys Glu Arg Phe Thr Val His Pro Ser Glu
            340                 345                 350

Val Pro Glu Ile Leu Ala Gly Arg Phe Asp Lys Ala Lys His Val Glu
        355                 360                 365

Lys Met Arg Ala Lys Gly Lys Ser Glu Lys Glu Val Glu Asp Trp Asp
    370                 375                 380

Ile Leu Val Thr Glu Val Cys Gln Ala Ile Asn Ser Lys Gln Leu Val
385                 390                 395                 400

Pro Thr Leu Arg Thr Gln Tyr Met Arg Thr Ala Phe Gln Ile Pro Phe
                405                 410                 415

Asp Ala Thr Val Arg Ile Ser Leu Asp Thr Asn Leu Cys Met Leu Thr
            420                 425                 430

Glu Thr Gly Arg Leu Gly Met Asp Gln Asp Arg Trp Phe Arg Asp Pro
        435                 440                 445

Ser Lys Pro Val Pro Arg Asn Glu Ile Thr Arg Phe Pro His Ala Val
    450                 455                 460

Leu Glu Val Lys Leu Gln Leu Lys Asp Glu Gly Ala Lys Pro Gln Trp
465                 470                 475                 480

Val Thr Asp Leu Leu Ser Ser Gly Ile Pro Arg Glu Val His Lys Phe
                485                 490                 495

Ser Lys Phe Ile His Gly Cys Ala Val Leu Leu Pro Glu Glu Val Gln
            500                 505                 510

Ala Met Pro Tyr Trp Ile Asp Asp Pro Ser Leu Arg Glu Ser Ile Ala
```

```
        515                 520                 525
Ala Ser Gly Ser Glu Asn Ile Leu Glu Pro Glu Ser Gly Lys Lys Gly
530                 535                 540

Gly Val Gly Gly Met Leu Ala His Met Leu Pro His Gly Lys Glu Gly
545                 550                 555                 560

Lys Glu Lys Ala Lys Thr Thr Ala Leu Ser Ala Ala Lys Arg Thr
            565                 570                 575

Pro Ala Pro Thr Pro Arg Arg Asp Ser Glu Thr Pro Leu Pro Ser Arg
            580                 585                 590

Val Ser Val Gly Ala Ser Lys Gly Lys Ala Trp Ser Ala Pro Leu Met
            595                 600                 605

Ala Ser Thr Glu Glu Glu Tyr Tyr Glu Asp Glu Glu Gly Pro Gly
        610                 615                 620

Cys Trp Glu Ser Met Cys Gly Gly Cys Phe Ala Trp Ala Ala Pro Pro
625                 630                 635                 640

Glu Ile Ser Ala Arg Met Ala Gln Gln Lys Val Glu Pro Lys Leu Phe
                645                 650                 655

Phe Ala Asn Glu Arg Thr Phe Ile His Trp Leu Asn Met Ala Val Thr
            660                 665                 670

Ile Ser Ser Leu Gly Ala Ala Val Leu Ala Phe Ser Pro Glu Asp Thr
        675                 680                 685

Val Ser Glu Leu Tyr Gly Ile Ile Leu Met Pro Val Ser Leu Leu Phe
        690                 695                 700

Ala Leu Tyr Ala Leu Asn Thr Tyr Ile Thr Arg Ser Ala Lys Ile Arg
705                 710                 715                 720

Thr Arg Glu Pro Thr Arg Trp Asp Asp Pro Met Gly Pro Val Leu Leu
                725                 730                 735

Gly Ser Ile Phe Thr Leu Ala Leu Thr Ala Gln Phe Leu Ile Lys Leu
            740                 745                 750

Ala His Val Leu Lys Gln Asp Glu Val
        755                 760

<210> SEQ ID NO 3
<211> LENGTH: 29
<212> TYPE: DNA
<213> ORGANISM: Artificial Sequence
<220> FEATURE:
<223> OTHER INFORMATION: primer

<400> SEQUENCE: 3
aaaggtaccg ccactcataa agagcataa                                    29

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
aaaggtacca aaaattgctc gcccacctc                                    29

<210> SEQ ID NO 5
<211> LENGTH: 20
<212> TYPE: DNA
<213> ORGANISM: Artificial Sequence
<220> FEATURE:
<223> OTHER INFORMATION: primer
```

```
<400> SEQUENCE: 5
aaaacgactg cgctgtctgc                                                    20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6 tgagtcccatt gctggctgct                                                   20

<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7
gttttcccag tcacgac                                                       17

<210> SEQ ID NO 8
<211> LENGTH: 17
<212> TYPE: DNA
<213> ORGANISM: Artificial Sequence
<220> FEATURE:
<223> OTHER INFORMATION: primer

<400> SEQUENCE: 8
caggaaacag ctatgac                                                       17

<210> SEQ ID NO 9
<211> LENGTH: 1769
<212> TYPE: DNA
<213> ORGANISM: Artificial Sequence
<220> FEATURE:
<223> OTHER INFORMATION: drug resistance gene

<400> SEQUENCE: 9
aagcaagacg gaacaagatg gcacgcgtct gcaacagacc ggctcgcgcc gaacgtgcct        60
cctgcttttc aacgatcctg cgaggtcaac caggatttgc tcgccgggac gatttcatcc       120
ccttatcaac gagcccttga ggctccaggc gtgcttccac accccagttg gtaacaggac       180
attggggcat cttgcctatc ttgtcttagt gccgaaagcc tcaacgacct cccatggggt       240
ctgctcaacg cctcaacctt gcagtaagga tccccgaggg caagacccgc aaagccttct       300
gtcgtcggac aaagcggagc gagggaacag gctcagctca accctcttga gagcccataa       360
gtgccccctg atctatcttc aacagtcttt ccctgtcaca agaaaaccca gctagttgac       420
caagttgcta gagctgacat ccttgtactt cgctctttct gtgctttacc tgattggaca       480
tggacagacc tccccttgct cttccttcta ggagcctggg ctctcgctct tgttctttcg       540
agagaccttt cccttgagtt gcgtatccag cgatcaagta tgaagagtgc tttcaaacct       600
agatacgttc tgcccagttc tcttgccctt ttccacacgt gctccacatc ttcacacgac       660
tcgcaccata cccgacgaaa ccctcaaaa catcgcaaca cttacatccc gctcgtgtcc        720
cacccccgat gccatatcct ctacagcagc atggccaagt tgaccagtgc cgttccggtg       780
ctcaccgcgc gcgacgtcgc cggagcggtc gagttctgga ccgaccggct cgggttctcc       840
cgggacttcg tggaggacga cttcgccggt gtggtccggg acgacgtgac cctgttcatc       900
```

```
agcgcggtcc aggaccaggt ggtgccggac aacaccctgg cctgggtgtg ggtgcgcggc      960
ctggacgagc tgtacgccga gtggtcggag gtcgtgtcca cgaacttccg ggacgcctcc     1020
gggccggcca tgaccgagat cggcgagcag ccgtgggggc gggagttcgc cctgcgcgac     1080
ccggccggca actgcgtgca cttcgtggcc gaggagcagg actaagcttc tgtggaagag     1140
ccagtggtag tagcagtagc agcagcagta gcagccgcag cactcagtgt ggcgcgaga      1200 gattgtccat cccttcttaa cctaccggaa gagaaataag gcctttctcc cgtagctgtc     1260
ttcgtttgtt tgtgctgatt gcttggtatg agagtgttga attcctgcat catgttttc     1320 tctgtagtcc tttcctaccc ccgtcatttt cttttctccc tggttcttct tttgtcaccc     1380 ttatttaca  taaaattttc tttgtttata gtgagaggaa ggtagagagg ggaaaacaag     1440
aacaacgaac gcaagcgtgt gaaggaggg cgaatagaag agaaacagat ctgttgagca     1500
ttgagagtgg agccggggga aaggcttgtg tgttgttttt gaaaaagttt gtttaaatca     1560
cgaatccgtt agttctcatg tgtacctctt tcactacatg tgatggagaa aacaaaagtg     1620
tgaggattaa ttgaagaaaa agaagagttc gacacgtcaa accgcccaaa agacgtcaca     1680
aagagaactt gattctcttt gccgtgttga tcttgtcttt tccccagct tttcttgcca      1740 cccgtggcac acgagatgga caagatcag                                       1769

<210> SEQ ID NO 10
<211> LENGTH: 4433
<212> TYPE: DNA
<213> ORGANISM: Artificial Sequence
<220> FEATURE:
<223> OTHER INFORMATION: NT7 vector

<400> SEQUENCE: 10
gacgaaaggg cctcgtgata cgcctatttt tataggttaa tgtcatgata ataatggttt       60
cttagacgtc aggtggcact tttcggggaa atgtgcgcgg aacccctatt tgtttatttt      120
tctaaataca ttcaaatatg tatccgctca tgagacaata accctgataa atgcttcaat      180
aatattgaaa aaggaagagt atgagtattc aacatttccg tgtcgccctt attccctttt      240
ttgcggcatt ttgccttcct gttttgctc acccagaaac gctggtgaaa gtaaaagatg      300
ctgaagatca gttgggtgca cgagtgggtt acatcgaact ggatctcaac agcggtaaga    360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga ccaccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc atttttaatt taaaaggatc taggtgaaga    1140
```

```
tcctttttga taatctcatg accaaaatcc cttaacgtga gttttcgttc cactgagcgt    1200
cagaccccgt agaaaagatc aaaggatctt cttgagatcc ttttttttctg cgcgtaatct   1260 gctgcttgca aacaaaaaaa ccaccgctac cagcggtggt ttgtttgccg gatcaagagc    1320
taccaactct ttttccgaag gtaactggct tcagcagagc gcagatacca aatactgttc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agctatgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg atttttgtga tgctcgtcag    1800
gggggcggag cctatggaaa aacgccagca acgcggcctt tttacggttc ctggccttttt   1860 gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcaccccca ggctttacac tttatgcttc    2160
cggctcgtat gttgtgtgga attgtgagcg gataacaatt tcacacagga aacagctatg    2220
acatgattac gaattcgagc tcggtaccaa gcaagacgga acaagatggc acgcgtctgc    2280
aacagaccgg ctcgcgccga acgtgcctcc tgcttttcaa cgatcctgcg aggtcaacca    2340
ggatttgctc gccgggacga tttcatcccc ttatcaacga gcccttgagg ctccaggcgt    2400
gcttccacac cccagttggt aacaggacat tggggcatct tgcctatctt gtcttagtgc    2460
cgaaagcctc aacgacctcc catggggtct gctcaacgcc tcaaccttgc agtaaggatc    2520
cccgagggca agaccgcaa agccttctgt cgtcggacaa gcggagcga gggaacaggc      2580 tcagctcaac cctcttgaga gcccataagt gccccctgat ctatcttcaa cagtcttcc     2640 ctgtcacaag aaaacccagc tagttgacca agttgctaga gctgacatcc ttgtacttcg    2700
ctctttctgt gctttacctg attggacatg gacagacctc cccttgctct tccttctagg    2760
agcctgggct ctcgctcttg ttctttcgag agacctttcc cttgagttgc gtatccagcg    2820
atcaagtatg aagagtgctt tcaaacctag atacgttctg cccagttctc ttgccctttt    2880
ccacacgtgc tccacatctt cacacgactc gcaccatacc cgacgaaacc cctcaaaaca    2940
tcgcaacact tacatcccgc tcgtgtccca ccccgatgc catatcctct acagcagcat     3000
ggccaagttg accagtgccg ttccggtgct caccgcgcgc gacgtcgccg gagcggtcga    3060
gttctggacc gaccggctcg ggttctcccg ggacttcgtg gaggacgact tcgccggtgt    3120
ggtccgggac gacgtgaccc tgttcatcag cgcggtccag gaccaggtgg tgccggacaa    3180
caccctggcc tgggtgtggg tgcgcggcct ggacgagctg tacgccgagt ggtcggaggt    3240
cgtgtccacg aacttccggg acgcctccgg gccggccatg accgagatcg cgagcagcc    3300 gtggggggcgg gagttcgccc tgcgcgaccc ggccggcaac tgcgtgcact cgtggccga    3360 ggagcaggac taagcttctg tggaagagcc agtggtagta gcagtagcag cagcagtagc    3420
agccgcagca ctcagtgttg gcgcgagaga ttgtccatcc cttcttaacc taccggaaga    3480
gaaataaggc cttctcccg tagctgtctt cgtttgtttg tgctgattgc ttggtatgag    3540
```

-continued

```
agtgttgaat tcctgcatca tgttttctc tgtagtcctt tcctaccccc gtcatttct    3600 tttctccctg gttcttcttt tgtcacccct attttacata aaattttctt tgtttatagt   3660
gagaggaagg tagagagggg aaaacaagaa caacgaacgc aagcgtgtga aaggagggcg   3720
aatagaagag aaacagatct gttgagcatt gagagtggag ccggggggaaa ggcttgtgtg  3780 ttgttttttga aaaagtttgt ttaaatcacg aatccgttag ttctcatgtg tacctctttc  3840
actacatgtg atggagaaaa caaaagtgtg aggattaatt gaagaaaaag aagagttcga   3900
cacgtcaaac cgcccaaaag acgtcacaaa gagaacttga ttctctttgc cgtgttgatc   3960 ttgtctttc ccccagcttt tcttgccacc cgtggcacac gagatggaca agatcagctg    4020
caggcatgca agcttggcac tggccgtcgt tttacaacgt cgtgactggg aaaaccctgg   4080
cgttacccaa cttaatcgcc ttgcagcaca tccccttc gccagctggc gtaatagcga     4140 agaggccccgc accgatcgcc cttcccaaca gttgcgcagc ctgaatggcg aatggcgcct  4200
gatgcggtat tttctcctta cgcatctgtg cggtatttca caccgcatat ggtgcactct   4260
cagtacaatc tgctctgatg ccgcatagtt aagccagccc cgacacccgc caacacccgc   4320
tgacgcgccc tgacgggctt gtctgctccc ggcatccgct tacagacaag ctgtgaccgt   4380
ctccgggagc tgcatgtgtc agaggttttc accgtcatca ccgaaacgcg cga          4433
```

<210> SEQ ID NO 11  
<211> LENGTH: 20  
<212> TYPE: DNA  
<213> ORGANISM: Artificial Sequence  
<220> FEATURE:  
<223> OTHER INFORMATION: primer

<400> SEQUENCE: 11

```
atggctgaat gtacccgtgt                                               20
```

<210> SEQ ID NO 12  
<211> LENGTH: 20  
<212> TYPE: DNA  
<213> ORGANISM: Artificial Sequence  
<220> FEATURE:  
<223> OTHER INFORMATION: primer

<400> SEQUENCE: 12

```
ctagacctca tcctgcttca                                               20
```

<210> SEQ ID NO 13  
<211> LENGTH: 4670  
<212> TYPE: DNA  
<213> ORGANISM: Nannochloropsis sp.  
<220> FEATURE:  
<221> NAME/KEY: CDS  
<222> LOCATION: 1042..2503  
<220> FEATURE:  
<221> NAME/KEY: intron  
<222> LOCATION: 2504..2682  
<220> FEATURE:  
<221> NAME/KEY: CDS  
<222> LOCATION: 2683..3503

<400> SEQUENCE: 13

```
tgattagttt cggcgtaaat gagagagagg gtttggcggg tggagtgaac gaagctatgg    60
aggtcgcgac gcgtgggagg ggtgaagggc cgcagctcga aggcgatggt gcaggcgagg   120
gtgtaccatt tggtggggtt ttgggattgg acttgaccag gtggttgtgg gtgcggagga   180
cgacgaggag gagcgccacg atgaacgggt ggcatggcag ggatgttgaa agcggctggg   240
```

```
gagcacagat gatgacgact ggggcaaaag caagttagtt attagtaatt gagctctctt      300
taagtgtgcg tagccctacg agtgtgagtg catgaggata gagaggggt  tagagtgtta      360 agggtgtcct cctgaaggaa gaagcgctag atttcacagg tagactctac aagcggttat      420
catcaaacca tttatggctg aatgtacccg tgtgtacgaa ggcgacttcg cttacttgac      480
aactgctttc gttcatgccc ccagtcagag agaaggatga atcctcgctc aaggaaacaa      540
gccactcata aagagcataa tgcttcccag cgaggccacc agccttacaa tttcgcgtga      600
caagcaaggc ggcgggatta cgggcactta tgtcagtccc actactttgt attataacac      660
tctctgcttg tcgcgcggat atgtattggg gaatcactga ttgcacgaac tcagatgacg      720
acggctctta ctgatgatac ttgcttcgtc gctgctcttg gcccctcac  aacattcgtt      780 cctaatcgaa tgtctcgcct ggtttccttc cgccagatca atgcatcact cacgttcctt      840
atatctcttg tcatagtccg gcgacatccc ttttgatagg aggacgtgcg gcgacggaga      900
aaacaggcgc aaaacagcc  cccagcctcc cctccccgct agcagcagga cagttagcac      960
cccagtagct acaagcgacg cccgcagcgc gtacattcgc ctccacaaaa gccttgtgct     1020
agaagccgca ccgctagcat catgaagttt ggtctgtatc tgcgcgagaa cgtggtggaa     1080
gaatggaagc aatactactt gcaatacgac aaactaaagc gaatgattcg cattctggcc     1140 gaagtgggaga gcaaagccat ggccccgaa cctaccttga cgggcaaggt tggcttttcg     1200
cttacggttc ctccgcctac caatgcagcg gcgcagcctc tcggccgtgc gggcaagggc     1260
atgggaggcg tgatggacgg agactcggat gatgaagatt cctcaggcgg cgacgaggcg     1320
gacgctgcgc ccgtgacgca cgagttattt ttcgatctgt tggagaagga aattcagaag     1380
gtacacaact tcaccgacag gaaagtgact gaaattaggg ccaaattgcg ggatgtggga     1440
aagagactga aaattggcac gatagaagtc gtgcccgggg ggcagccttt ggagataggg     1500
gatgctgtgc ggaaggaggt ggacgaggtg ggcgagcaat ttttgcggtt ggaaaagtac     1560
gtgaacctaa attcactgg  gtttcacaag attttgaaga agcatgacag gtggttgacg     1620
aacccgtgtc ggactttta  tttgcagagg ctgcagaacc ataattggac gcaaggcgat     1680
tattcggatg tggtggtgac gatgagccag atctggtcgg cgttgagggg ggatgttgct     1740
cctgagggga ccgcgacgga gagtcaggag ttcgtgcgga gcactaccaa gtactggatt     1800
caagacgagg atatttctca gttgaagtgg tttgtgctgc agcacttgcc ggtgttgctc     1860
caagagagca tgggaaccaa atccgattct cagttggtga attcggtgta cttggacaat     1920
gccacgttag agctgtataa aggacggttg gacaagacac caggagcgat cgcggttcga     1980
ttcaggtggt atgggtccgg tactcccgag cttgttttg  tggagcggaa gacccaccgc     2040
gaggcatgga ctgcgagat  gagcgtgaaa gaacgcttca cggtgcatcc ttcggaagta     2100
ccggagattt tggcgggcag gttcgacaag gccaagcatg tggagaagat gcgggcgaag     2160
gggaaaagcg agaaggaggt ggaggattgg gacatcttgg tgacgaggt  gtgccaggcg     2220 attaacagca agcagcttgt cccgacgctg aggacgcagt acatgcggac ggcctttcaa     2280
attccgttcg atgccacggt gcggatcagc ctggacacga atctgtgcat gctgacggaa     2340
acggggcggt tgggcatgga ccaggacagg tggttccgag acccgagcaa gccggtgccg     2400
cggaatgaga tcacccgctt tccccacgcc gtgcttgagg tgaagctgca attaaaggac     2460
gagggggcca agccgcagtg ggtcacggat ttgttgagtt caggtacgtg gtgaagaaga     2520
ggttgctcat gttgtgcgtg cttctccccc gcttttctc  cccttccga  ttcgtgtgtg     2580
```

-continued

```
ctttccccct tttactagta tccgatgtat cttctttcag ccctctcctc ctccttttct    2640
caaatgatca tccgtttctc cctccctccc tcgctgcccc aggcatcccc cgcgaagtcc    2700
acaagttttc taagtttatc cacggatgcg ccgtcctgct gccagaggaa gtgcaggcca    2760
tgccctactg gatcgacgac ccctcattgc gcgagtccat tgctgcctcg ggtccgaga    2820
atatcttgga accggagagt gggaagaagg gagggtggg aggaatgctg gcgcacatgc    2880
tgccgcatgg gaaagaaggg aaggagaagg cgaaaacgac tgcgctgtct gcagcagcaa    2940
aacgaacgcc cgccccgaca ccaaggaggg acagcgagac accgcttcct tcaagggtgt    3000
cagtgggtgc aagtaaagga aaggcatggt cggcgccttt gatggcctcc acggaggagg    3060
agtattatga ggacgaggag ggcgggcctg gttgttggga gagtatgtgt ggagggtgtt    3120
tcgcctgggc agctccaccc gagatttcgg cacggatggc gcagcagaaa gtggagccca    3180
agctgttctt tgcgaatgaa cggacattta tccattggtt gaatatggcc gtgacgattt    3240
cttccctggg cgcggcggtc ttggccttct ccccgagga caccgtgagt gagctgtacg    3300
gaattatctt gatgcccgtg tcgttgttat tcgctttgta cgcccctcaac acctacatca    3360
cgcgaagcgc gaagatccgg acgcgggagc cgacgaggtg ggatgacccg atggggcccg    3420
tgcttttggg gagtatcttc acattggcgt tgacagctca gttttttgatt aagttggccc    3480
atgtgttgaa gcaggatgag gtctaggtgg agggagggag agagagggg agggaggtat    3540
ggtgggata aggtaggtag gcggtcacgg atacaattga aggggattgt agagggaatt    3600
cgaggcgatg ggggagggag agaaagagag gaagagggga agttttcttt tattaaataa    3660
gcaagggata tgctgggatg atatatcgag gtacgtgttt agaaagaggg ggttcaaggg    3720
cgagatcgac cgggaaactt cgcggcagct cctaccccc caatacaatc gcactgggag    3780
aaagaggagg agacaatggt ggttataatt atgataattg tgcatgcacg cacgggcggt    3840
agctgaccga cagagcgggt agaaaaacag acttatttac atggcaatag ggggttttga    3900
gaacacgacg tgaaatagcc gaggagtaag ggatggaggg agggagggag gggtggaaga    3960
taagagagtg tagtttgggt agatggaaag cgccaccttg tcaaagctct attcaaagat    4020
ttcatcgtcg gagctgcagc agccagcaag ggactcactg ggctctattt ctttcatctt    4080
ctctgctctt gttcacctcc ctattttggg attgattctg gctattgaaa gaagtctatc    4140
ggtctttatt ataaccccta ctaatttggg ttctttctgt cccacatctg ctacatgccc    4200
cttcacctac acatacacct ctccttcctt tgccccctcc ctccttccat ccctattccc    4260
gctcgatcct cccctgcctg accgcctcgt ccatcgcccc taaaaacacg tccagcccca    4320
ccgtccgagg tgctgccatc agcgaatggg ccagcaaagg caatttccgc aggccacgtc    4380
cactcatccc ctccgtgcgt tcaaccaact ggagtagtag ctgccttacc cctggagcct    4440
gctgctgctg ccgctgctgg ttgtgctgtt ggtgctgttg gtgctgttgg tgctgaggag    4500
gaagggaagt ggaataagtt gcagcagcaa gggagggaag caactcaacg cgttcaggca    4560
gatgcatgcg ggggatgatg accccacaac gcatgagctc cacaagggcg gaacgaagga    4620
tggcataccg cccctcggga cggggcaggc ccacgtggag cttttaagtcg              4670
```

<210> SEQ ID NO 14
<211> LENGTH: 721
<212> TYPE: PRT
<213> ORGANISM: Saccharomyces cerevisiae

<400> SEQUENCE: 14

Met Lys Phe Gly Glu His Leu Ser Lys Ser Leu Ile Arg Gln Tyr Ser

-continued

```
1               5                   10                  15
Tyr Tyr Tyr Ile Ser Tyr Asp Asp Leu Lys Thr Glu Leu Glu Asp Asn
                20                  25                  30
Leu Ser Lys Asn Asn Gly Gln Trp Thr Gln Glu Leu Glu Thr Asp Phe
                35                  40                  45
Leu Glu Ser Leu Glu Ile Glu Leu Asp Lys Val Tyr Thr Phe Cys Lys
        50                  55                  60
Val Lys His Ser Glu Val Phe Arg Arg Val Lys Glu Val Gln Glu Gln
65                  70                  75                  80
Val Gln His Thr Val Arg Leu Leu Asp Ser Asn Asn Pro Thr Gln
                85                  90                  95
Leu Asp Phe Glu Ile Leu Glu Glu Leu Ser Asp Ile Ile Ala Asp
                100                 105                 110
Val His Asp Leu Ala Lys Phe Ser Arg Leu Asn Tyr Thr Gly Phe Gln
                115                 120                 125
Lys Ile Ile Lys Lys His Asp Lys Lys Thr Gly Phe Ile Leu Lys Pro
        130                 135                 140
Val Phe Gln Val Arg Leu Asp Ser Lys Pro Phe Phe Lys Glu Asn Tyr
145                 150                 155                 160
Asp Glu Leu Val Val Lys Ile Ser Gln Leu Tyr Asp Ile Ala Arg Thr
                165                 170                 175
Ser Gly Arg Pro Ile Lys Gly Asp Ser Ser Ala Gly Gly Lys Gln Gln
                180                 185                 190
Asn Phe Val Arg Gln Thr Thr Lys Tyr Trp Val His Pro Asp Asn Ile
                195                 200                 205
Thr Glu Leu Lys Leu Ile Ile Leu Lys His Leu Pro Val Leu Val Phe
        210                 215                 220
Asn Thr Asn Lys Glu Phe Glu Arg Glu Asp Ser Ala Ile Thr Ser Ile
225                 230                 235                 240
Tyr Phe Asp Asn Glu Asn Leu Asp Leu Tyr Tyr Gly Arg Leu Arg Lys
                245                 250                 255
Asp Glu Gly Ala Glu Ala His Arg Leu Arg Trp Tyr Gly Met Ser
                260                 265                 270
Thr Asp Thr Ile Phe Val Glu Arg Lys Thr His Arg Glu Asp Trp Thr
        275                 280                 285
Gly Glu Lys Ser Val Lys Ala Arg Phe Ala Leu Lys Glu Arg His Val
        290                 295                 300
Asn Asp Phe Leu Lys Gly Lys Tyr Thr Val Asp Gln Val Phe Ala Lys
305                 310                 315                 320
Met Arg Lys Glu Gly Lys Lys Pro Met Asn Glu Ile Glu Asn Leu Glu
                325                 330                 335
Ala Leu Ala Ser Glu Ile Gln Tyr Val Met Leu Lys Lys Leu Arg
                340                 345                 350
Pro Val Val Arg Ser Phe Tyr Asn Arg Thr Ala Phe Gln Leu Pro Gly
                355                 360                 365
Asp Ala Arg Val Arg Ile Ser Leu Asp Thr Glu Leu Thr Met Val Arg
        370                 375                 380
Glu Asp Asn Phe Asp Gly Val Asp Arg Thr His Lys Asn Trp Arg Arg
385                 390                 395                 400
Thr Asp Ile Gly Val Asp Trp Pro Phe Lys Gln Leu Asp Asp Lys Asp
                405                 410                 415
Ile Cys Arg Phe Pro Tyr Ala Val Leu Glu Val Lys Leu Gln Thr Gln
                420                 425                 430
```

```
Leu Gly Gln Glu Pro Pro Glu Trp Val Arg Glu Leu Val Gly Ser His
            435                 440                 445
Leu Val Glu Pro Val Pro Lys Phe Ser Lys Phe Ile His Gly Val Ala
450                 455                 460
Thr Leu Leu Asn Asp Lys Val Asp Ser Ile Pro Phe Trp Leu Pro Gln
465                 470                 475                 480
Met Asp Val Asp Ile Arg Lys Pro Pro Leu Pro Thr Asn Ile Glu Ile
                485                 490                 495
Thr Arg Pro Gly Arg Ser Asp Asn Glu Asp Asn Asp Phe Asp Glu Asp
                500                 505                 510
Asp Glu Asp Asp Ala Ala Leu Val Ala Ala Met Thr Asn Ala Pro Gly
            515                 520                 525
Asn Ser Leu Asp Ile Glu Glu Ser Val Gly Tyr Gly Ala Thr Ser Ala
            530                 535                 540
Pro Thr Ser Asn Thr Asn His Val Val Glu Ser Ala Asn Ala Ala Tyr
545                 550                 555                 560
Tyr Gln Arg Lys Ile Arg Asn Ala Glu Asn Pro Ile Ser Lys Lys Tyr
                565                 570                 575
Tyr Glu Ile Val Ala Phe Phe Asp His Tyr Phe Asn Gly Asp Gln Ile
            580                 585                 590
Ser Lys Ile Pro Lys Gly Thr Thr Phe Asp Thr Gln Ile Arg Ala Pro
            595                 600                 605
Pro Gly Lys Thr Ile Cys Val Pro Val Arg Val Glu Pro Lys Val Tyr
            610                 615                 620
Phe Ala Thr Glu Arg Thr Tyr Leu Ser Trp Leu Ser Ile Ser Ile Leu
625                 630                 635                 640
Leu Gly Gly Val Ser Thr Thr Leu Leu Thr Tyr Gly Ser Pro Thr Ala
                645                 650                 655
Met Ile Gly Ser Ile Gly Phe Phe Ile Thr Ser Leu Ala Val Leu Ile
            660                 665                 670
Arg Thr Val Met Val Tyr Ala Lys Arg Val Val Asn Ile Arg Leu Lys
            675                 680                 685
Arg Ala Val Asp Tyr Glu Asp Lys Ile Gly Pro Gly Met Val Ser Val
            690                 695                 700
Phe Leu Ile Leu Ser Ile Leu Phe Ser Phe Phe Cys Asn Leu Val Ala
705                 710                 715                 720
Lys

<210> SEQ ID NO 15
<211> LENGTH: 793
<212> TYPE: PRT
<213> ORGANISM: Trypanosoma brucei

<400> SEQUENCE: 15

Met Pro Phe Ser Lys Ala Trp Arg Ser Ala Val Tyr Pro Asp Phe Arg
1               5                   10                  15
Glu Gln Gly Ala Tyr Ile Asn Tyr Lys Ala Thr Lys Asp Thr Leu His
                20                  25                  30
Arg Met Lys Glu Asp Ile Ala Asn Pro Ala Thr Pro Asp Glu Leu Tyr
            35                  40                  45
Asn Ser Leu Leu Met Gln Lys Ala Thr Val Tyr Lys Trp Cys Glu Asn
        50                  55                  60
Lys Val Lys Glu Leu Gln Met Met Ala Glu Ala Leu Met Lys Ala Ser
65                  70                  75                  80
```

```
Asp Tyr Leu Ser Glu Glu Thr Pro Thr Asn Met Ser Met Val Phe
            85                  90                  95

Ser Met Val Gly Ser Ser Glu Ala Lys Tyr Leu Pro Pro Ser Asp Ala
            100                 105                 110

Arg Arg Val Ala Asp Ala Ile Thr Tyr Glu Leu Leu Arg Phe Val Glu
            115                 120                 125

Cys Arg Asn Leu Asn Thr Asp Thr Ile Glu His Ile Ile Ala Arg Met
130                 135                 140

Tyr Arg Tyr Ala Val Leu Gly Pro Thr Gly Asp Arg Trp Lys Asn Ile
145                 150                 155                 160

Asn Lys Glu Tyr Asp Tyr His Ala Leu Ser Ile Asp Glu Ile Phe Phe
                165                 170                 175

Met Leu Ser Lys Val Tyr Glu His Val Asn Glu Val Glu Ser Met Arg
            180                 185                 190

Arg Asp Gly Arg Ser Ser Ile Pro Cys Gly Thr Val Gly Ser Gln Val
            195                 200                 205

Phe Asp Arg Arg Ser Val Lys Tyr Trp Val His Met Gln Asp Leu Pro
            210                 215                 220

Phe Val Ile Ala Arg Ile Ile Pro His Leu Pro Leu Ser Thr Phe Gln
225                 230                 235                 240

Asp Thr Tyr Ala Met Ser Lys Glu Arg Gly Val Pro Phe Thr Leu Gly
                245                 250                 255

Ser Pro Ile Ser Ser Val Tyr Tyr Asp Asn Asp Lys Phe Leu Leu Tyr
            260                 265                 270

His Arg Arg Leu Glu Arg Leu Asp Gly Ala Thr Leu Ile Arg Met Arg
            275                 280                 285

Trp Tyr Gly Arg Pro Leu Asp Ser Asp Trp Asn Lys Leu Glu Ser Lys
            290                 295                 300

Asp Ser Val Phe Met Glu Ile Lys Val His His Glu Ala Trp Ser Gly
305                 310                 315                 320

Glu Arg Ser Asn Lys Arg Arg Phe Ala Leu Lys Glu Lys Asp Val Asp
                325                 330                 335

Ala Tyr Ile Arg Gly Asp Leu Ser Leu Lys Pro Ala Leu Glu Lys Leu
            340                 345                 350

Arg Ser Lys Asn Ala Ser Glu Ala Glu Gln Glu Lys Phe Met Ser Leu
            355                 360                 365

Ala Thr Glu Ile Leu Thr Lys Ile His Ala Tyr Asp Leu Lys Pro Val
            370                 375                 380

Leu Arg Thr Gln Cys Gln Arg Ala Ala Phe Gln Cys Gly Leu Asp Gln
385                 390                 395                 400

Ser Ile Arg Ile Ser Ile Asp Thr Asp Leu Arg Val Val Ala Glu Asp
                405                 410                 415

Phe Gly Leu Ser His His Trp Arg Tyr Asn Gly Ala Asp Ala Pro Leu
            420                 425                 430

Ser His Phe Pro Tyr Ala Val Val Glu Val Lys Leu Gln Cys Ala Glu
            435                 440                 445

Asn Glu Arg Ile Ala Pro Trp Ile Glu Glu Leu Met Asn Cys Arg Tyr
450                 455                 460

Met Glu Ser Val Pro Lys Phe Ser Lys Tyr Ala His Gly Ile Ala Thr
465                 470                 475                 480

Leu Tyr Gly His Thr Pro Phe Ile Lys Met Val Pro Tyr Trp Met Pro
                485                 490                 495
```

-continued

```
Gln Leu Asp Ile Asp Ile Arg Ala Ser Thr Lys Pro Glu Tyr Asn Gln
            500                 505                 510

Trp Asp Pro Thr Ile Gly Ile Ala Ser Gly Cys Trp Glu Arg Thr Thr
        515                 520                 525

Asp Arg Val Ile Phe Gly Thr Gly His Ala Gln Thr Gln Thr Val Gly
    530                 535                 540

Ala Ser Glu Ala Arg Phe Leu Pro Arg Thr Asp Cys Leu Arg Thr Tyr
545                 550                 555                 560

Gln Arg Val Leu Lys Ala Ile Lys Arg Gly Ala His Met Asn Ser Val
                565                 570                 575

Ala Pro Thr Met Ser Pro Thr Asp Arg Pro Pro Ser Asp Glu Lys Lys
            580                 585                 590

Leu Thr Glu Gln Gln Glu Leu Ala Pro Val Val Gln Tyr Asp Thr Asp
        595                 600                 605

Arg Arg His Lys Ala Tyr Thr Ala Phe His Leu Tyr Pro Tyr Cys Glu
    610                 615                 620

Asp Gly Val Glu Ser Leu Cys Phe Thr Ser Thr Gly Gly Lys His Val
625                 630                 635                 640

Ala Ala Glu Val Phe Ser Gly Leu Ile Pro Trp Gln Thr Gly Lys Arg
                645                 650                 655

Ile Arg Val Pro Gln Lys Tyr Asp Pro Lys Thr Leu Leu Thr Ser Glu
            660                 665                 670

Arg Phe Met Val Lys Trp Ala Glu Gln Ala Thr Arg Val Gly Val Val
        675                 680                 685

Gly Leu Ala Val Ile Arg Phe Gly Asn Ser Met Ser Leu Pro Asn Asp
    690                 695                 700

Met Val Ala Val His Ser Phe Trp Arg Ala Asn Phe His Ile Val Leu
705                 710                 715                 720

Gly Ser Leu Met Val Val Ala Glu Cys Val Leu Val Tyr Ala Tyr
                725                 730                 735

Val Thr Phe Lys Ser Arg Ser Arg Arg Val Tyr Ala Arg Arg Lys Ile
            740                 745                 750

Arg Tyr Asp Asp Arg Arg Gly Pro Val Ala Leu Thr Phe Val Ile Leu
        755                 760                 765

Ala Val Ile Leu Ile Thr Val Met Met His Val Met Val Arg Tyr Gly
    770                 775                 780

Pro Met Leu Thr Gly Ser Asp Thr Phe
785                 790
```

MICROORGANISM AND METHOD FOR PRODUCING TRIACYLGLYCEROL

The contents of the electronic sequence listing (Name: sequence-listing.txt; Date of Creation: May 9, 2022; and Size: 36,157 bytes) is herein incorporated by reference in its entirety.

TECHNICAL FIELD

The present disclosure relates to a microorganism and a method for producing triacylglycerol.

BACKGROUND ART

Essential macro-elements such as nitrogen and phosphorus are frequently depleted in a growth environment. Therefore, higher plants and microorganisms such as algae have developed various response mechanisms for adapting themselves to deficiency of such inorganic nutrient salts. It is known that deficiency of nutrient salts causes, in many algae, proliferation decrease, chloroplast reduction, and accumulation of fats and oils such as triacylglycerol (hereinafter also referred to as "TAG").

In particular, nitrogen deficiency rapidly deteriorates photosynthesis function, and stops cell proliferation. On the other hand, it is known that, in a case of phosphorus deficiency, chloroplast function is comparatively retained, and membrane lipid remodeling such as phospholipid reduction and glycolipid increase occurs in accordance with TAG accumulation.

On the basis of these findings, for example, Patent Literature 1 discloses a method for accumulating TAG in alga cells in which an alga produced by introducing, into an alga belonging to *Chlamydomonas reinhardtii*, a TAG synthetic enzyme gene to which a SQD2 promoter derived from the alga has been added is cultured under phosphorus deficient conditions.

In this manner, from the viewpoint of sustainable biomass production using a microorganism, phosphorus deficiency can be regarded as a promising condition for inducing accumulation of fats and oils such as TAG replaceable with nitrogen deficiency, but there are many unexplained points in molecular mechanism of phosphorus deficiency response in a microorganism.

In, for example, a higher plant, it has been revealed, by a method such as gene knockout, that a protein having SPX domain (hereinafter also referred to as "SPX protein") is involved in phosphorus deficiency response and its control (see, for example, Non Patent Literature 1), but there is no reports on the analysis of such mechanism in an alga.

Besides, through comprehensive gene expression analysis of phosphorus deficiency response of *Nannochloropsis*, that is, one of microalgae, No_663 gene is mentioned as one of response genes having SPX domain (see, for example, Non Patent Literature 2), but the relationship between No_663 gene and the accumulation of fats and oils such as TAG is not mentioned.

CITATION LIST

Patent Literature

Patent Literature 1: Japanese Patent No. 5988212

Non Patent Literature

Non Patent Literature 1: Liu et al., Open Biol. 2018-Jan. 3; 8 (1): 170231

Non Patent Literature 2: Muhlroth et al., Plant Physiol. 2017-Oct. 19; 175(4): 1543-1559

SUMMARY OF INVENTION

Technical Problem

Under these circumstances, an object of the present disclosure is to provide a microorganism capable of highly accumulating TAG under phosphorus deficient conditions, and a method for producing TAG using the microorganism.

Solution to Problem

A microorganism of the present disclosure is a microorganism having at least one SPX gene encoding SPX protein responsive to phosphorus deficiency, characterized in that a function of the SPX protein is decreased or lost by introducing gene mutation into the SPX gene.

Advantageous Effects of Invention

According to the present disclosure, a microorganism capable of highly accumulating TAG under phosphorus deficient conditions, and a method for producing TAG using the microorganism can be obtained.

BRIEF DESCRIPTION OF DRAWINGS

FIG. 2 is a diagram illustrating results of comparison in amino acid sequence among SPX2 protein of *Nannochloropsis* and VTC4 protein of yeast and *Trypanosoma*. VTC4 protein of yeast (SEQ ID NO: 14), SPX2 protein of *Nannochloropsis* (SEQ ID NO: 13), and VTC4 protein of *Trypanosoma* (SEQ ID NO: 15) are successively illustrated in a downward direction.

DESCRIPTION OF EMBODIMENT

Now, an embodiment of the present disclosure will be described in detail based on the accompanying drawings. It is noted that the following description of a preferred embodiment is substantially merely illustrative, and does not intend to limit the present disclosure, and the application or use thereof.

Herein, SPX protein means a protein having SPX domain as described above. As a protein having SPX domain, those involved in absorption, transport and storage of inorganic phosphate in a eukaryote, and signal transduction for controlling these are known. SPX domain consists of 150 to 380 amino acid residues, and in regard to phosphorus deficiency response, is found at an amino terminal (N terminal) of a protein such as an inorganic phosphate transporter, a signal transduction protein involved in inorganic phosphate response, or a polyphosphate synthetic enzyme/vacuolar transporter chaperone (VTC) complex (Wild et al., Science 2016-May 20; 352 (6288): 986-990). Besides, herein, a gene encoding SPX protein is designated as SPX gene.

(Embodiment of Present Disclosure)

Figure 1A:
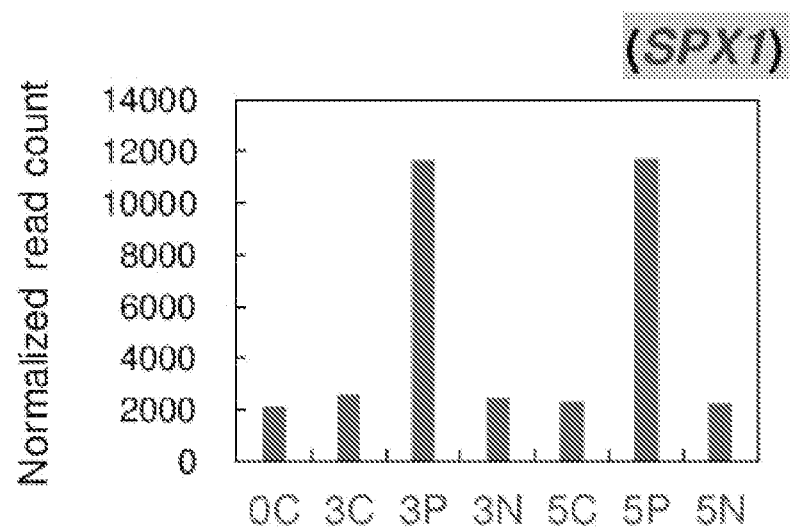
FIG. 1 is a diagram illustrating gene expression levels of SPX1 gene (FIG. 1A) and SPX2 gene (FIG. 1B) in various media analyzed by an RNA sequencing method. In the diagram, "0C" indicates a time of starting culture, "3C" indicates day 3 of culture in a control medium (F2N), "3P" indicates day 3 of culture in a phosphorus deficient medium (—P), "3N" indicates day 3 of culture in a nitrogen deficient medium (—N), "5C" indicates day 5 of culture in F2N, "5P" indicates day 5 of culture in —P, and "5N" indicates day 5 of culture in —N.
Figure 1B:
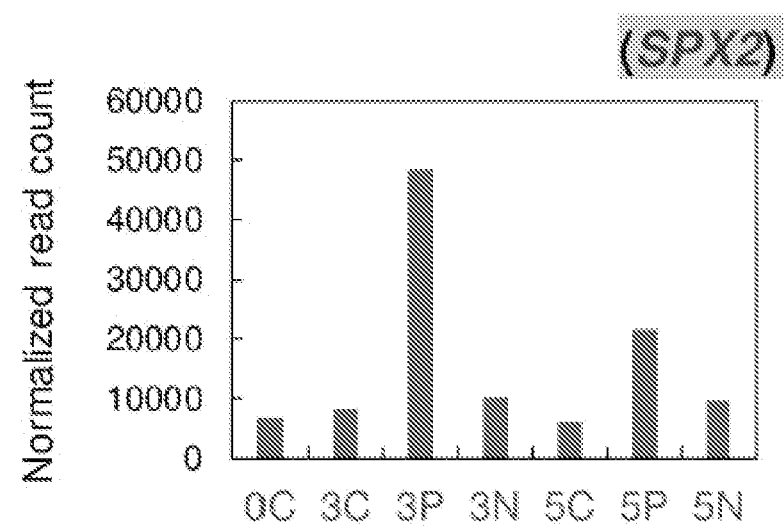

In consideration of the aforementioned observation, the present inventors comprehensively searched, by using *Nannochloropsis*, that is, one of microalgae highly accumulating TAG, a group of genes that are specifically increased in expression under inorganic phosphate deficient conditions. As a result, as illustrated in FIGS. 1A and 1B, two genes SPX1 gene (SEQ ID NO: 1) and SPX2 gene (SEQ ID NOS: 2 and 13), respectively, belonging to SPX gene family known to be involved in sensing and signaling of inorganic phosphate in yeast, a higher plant or the like were found. It is understood, in FIGS. 1A-1B, that both SPX1 gene and SPX2 gene are superiorly increased in expression level of the genes under phosphorus deficient conditions as compared with that in a control medium or under nitrogen deficient conditions. It is noted that the media used here are the same media as used in examples described below.

It can be presumed, based on the results, that the phosphorus deficiency response of a microorganism is enhanced by functional knockout of a homolog of SPX gene. As described above, one of representative phosphorus deficiency responses exhibited by an alga is accumulation of fats and oils such as TAG, and therefore, it is presumed that the functional knockout of SPX gene can be used for production increase of a biofuel or a useful high-value added lipid.

Based on these findings, the present inventors attempted to produce knockout strains of SPX1 gene and SPX2 gene by a method described in the examples described below. As a result, the gene knockout strain of SPX1 gene could not be obtained, and hence it is presumed to be essential for growth of *Nannochloropsis*. On the other hand, the knockout strain of SPX2 gene was obtained. The present disclosure is based on experimental finding that the SPX2 gene knockout strain accumulates TAG under phosphorus deficient conditions at a significantly high level as compared with a control strain.

SPX1 gene and SPX2 gene of *Nannochloropsis* found by the present inventors are both SPX genes encoding SPX protein responsive to phosphorus deficiency. The amino acid sequence from SPX1 gene is as set forth in SEQ ID NO: 1. The amino acid sequence of SPX2 gene and its genomic DNA sequence are respectively as set forth in SEQ ID NOS: 2 and 13. Positions 1042-2503 and positions 2683-3503 in SEQ ID NO: 13 are a portion corresponding to SEQ ID NO: 2 (it is noted that positions 2504-2682 in SEQ ID NO: 13 are a portion not translated into a protein (intron)).

Figure 2:
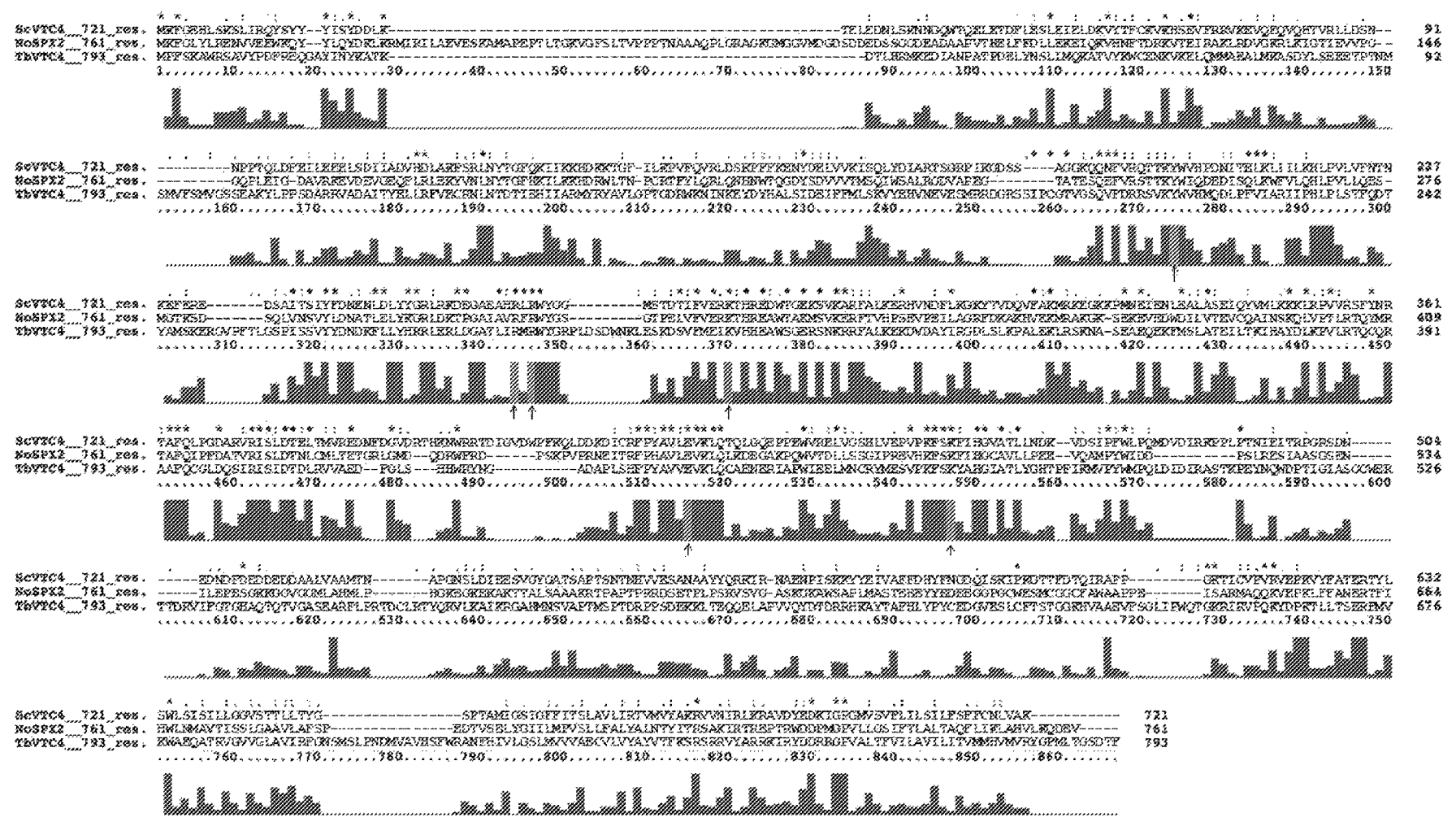

As illustrated in FIG. 2, with regard to SPX2 gene from which a gene knockout strain was produced, VTC4 gene of yeast, that is, one of genes encoding a VTC complex having been proved to have polyphosphate synthesis activity (Hothorn et al., Science 2009-Apr. 24; 324(5926): 513-516, SEQ ID NO: B3LQ90), VTC4 gene of *Trypanosoma*, that is, a parasite, (Lander et al., J. Biol. Chem. 2013 Nov. 22; 288(47): 34205-34216, SEQ ID NO: Q382V9) and amino acid sequences of proteins encoded by these genes were compared, resulting in finding homology therebetween.

Herein, a value of "homology" can be calculated by using a homology search program known to those skilled in the art. For example, it can be calculated by using a default (initially set) parameter in homology algorithm BLAST (basic local alignment search tool) of NCBI. Besides, the term "homology" means preferably 40% or more homology, more preferably 50% or more homology, and further preferably 60% or more homology under the aforementioned condition in BLAST.

Besides, SPX2 protein is regarded as an amino acid residue, shown with an arrow in FIG. 2, essential for expression of normal polyphosphate synthesis activity in VTC4 protein of yeast, and an amino acid residue conserved in VTC4 protein of *Trypanosoma* is also conserved therein.

Figure 11:
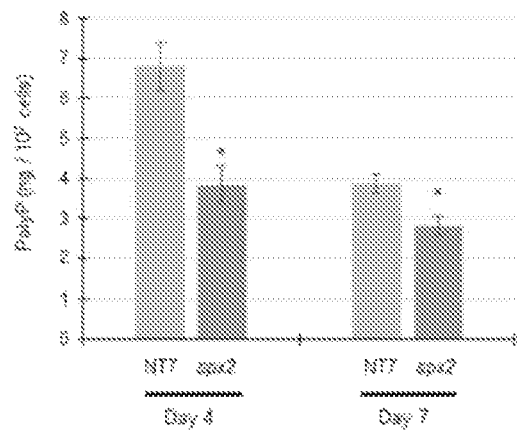
FIG. 11 is a diagram illustrating amounts of polyphosphate per cell obtained 4 days and 7 days after starting the culture of the control strain (NT7) and the SPX2 gene knockout strain (spx2) in F2N medium.

Furthermore, as illustrated in FIG. 11, it was found that knockout of SPX2 gene causes reduction of the amount of polyphosphate in a cell.

Accordingly, it is predicted that SPX2 gene encodes a protein having polyphosphate synthesis activity similar to that of VTC4 gene of yeast and VTC4 gene of *Trypanosoma*.

A microorganism of the present disclosure has at least one SPX gene. In other words, the microorganism may have one (one type of) SPX gene, or may have a plurality of (two or more types of) SPX genes. Incidentally, it was found by the present inventors that *Nannochloropsis* has at least two SPX genes, that is, SPX1 gene and SPX2 gene, as described above.

Besides, in the microorganism of the present disclosure, the function of SPX protein is decreased or lost by introducing gene mutation into SPX gene.

The term "to introduce gene mutation into SPX gene" means, for example, that one to several amino acids are deleted, replaced and/or added in the amino acid sequence from SPX gene. The term "one to several" is not especially limited as long as the function of SPX protein is thus decreased or lost, and may be, for example, one, or a total number in the amino acid sequence from SPX gene encoding SPX protein. Besides, the term "to delete, replace and/or add" embraces not only artificial mutation but also naturally occurring mutation (such as a mutant or a variant) caused by an individual difference, or a difference based on species or genus. Incidentally, gene mutation may be introduced into SPX gene by deleting, replacing and/or adding one to several nucleotide sequences of SPX gene. Besides, the term "mutation" embraces knockout of the gene encoding SPX protein.

The term "function of SPX protein is decreased or lost" means that the function of SPX protein is decreased or lost (disrupted) by introducing gene mutation into SPX gene, for example, an amino acid necessary for the activity is mutated even if the expression of the SPX protein is not suppressed or eliminated. In other words, it means that the function of SPX protein is suppressed (a state where the function is not completely lost) or made defective (the function is disrupted) by introducing gene mutation into SPX gene even if the expression of the SPX protein itself is normal.

With regard to, for example, SPX2 protein, it is predicted that the function of the SPX2 protein is decreased or lost when mutation is introduced into at least one of the following amino acid residues (amino acid residues shown with arrows in FIG. 2) corresponding to, as described above, an amino acid residue essential for the expression of normal polyphosphate synthesis activity in VTC4 protein of yeast: K250 (lysine at position 250 in SEQ ID NO: 2), R313 (arginine at position 313 in SEQ ID NO: 2), R315 (arginine at position 315 in SEQ ID NO: 2), K330 (lysine at position 330 in SEQ ID NO: 2), E466 (glutamic acid at position 466 in SEQ ID NO: 2), and K498 (lysine at position 498 in SEQ ID NO: 2). It is presumed that the SPX2 gene knockout strain having the function of SPX2 protein thus decreased or lost accumulates TAG at a significantly high level under phosphorus deficient conditions as compared with a control strain.

Here, SPX protein responsive to phosphorus deficiency is regarded to be widely present in microorganisms, particularly in algae. Therefore, the function of SPX protein may be a function conventionally known in various microorganisms, or may be a novel function found in future. For example, it is predicted that the function of SPX protein expressed by SPX2 gene found by the present inventors is polyphosphate synthesis activity as described above.

Incidentally, the function of SPX protein may be decreased or lost by suppressing or eliminating the expression of the SPX protein through introduction of gene mutation into SPX gene. Here, the term "to suppress the expression of SPX protein" means that the function of the SPX protein is decreased (reduced) or lost (made defective) because the expression level of SPX gene encoding the SPX protein is 50% or less (the expression level of SPX gene is suppressed to 50% or less). Besides, the term "to eliminate the expression of SPX protein" means that the function (activity) of the SPX protein is lost because the expression level of SPX gene encoding the SPX protein is 0% (the expression level of the SPX gene is suppressed by 100%).

As the microorganism, any of algae belonging to the genus *Chlamydomonas*, the genus *Nannochloropsis*, the genus *Microchloropsis*, the genus *Pseudochoricystis*, the genus *Phaeodactylum*, the genus *Ostreococcus*, the genus *Cyanidioschyzon*, the genus *Klebsormidium*, the genus *Chlorokybus*, the genus *Spirogyra*, the genus *Chara*, the genus *Coleochaete*, and the genus *Chlorella* can be used. Here, the genus *Microchloropsis* is a genus established by classifying a part of the genus *Nannochloropsis* as a different genus, and some algae may be redundant therein in some cases.

Among these organisms, algae belonging to the genus *Nannochloropsis* and the genus *Microchloropsis* that can accumulate fats and oils alone up to 60% at maximum of the dry weight and have particularly high fats and oils accumulation ability among algae are preferred. Besides, algae belonging to the genus *Nannochloropsis* and the genus *Microchloropsis* have the following advantages in addition to the fats and oils accumulation ability:

(1) Fatty acid compositions of accumulated fats and oils have a distribution mainly having a carbon number of 16, and hence they are suitable for production of a fuel equivalent to light oil.

(2) Depending on purification conditions and purification method, a liquid fuel such as a fuel equivalent to gasoline can be produced.

(3) Since cells are small and rapidly grow, high density culture can be performed.

(4) There is a low possibility of contamination.

An example of algae belonging to the genus *Chlamydomonas* includes *Chlamydomonas reinhardtii*. Examples of algae belonging to the genus *Nannochloropsis* include *Nannochloropsis oculata*, *Nannochloropsis oceanica*, *Nannochloropsis granulata*, *Nannochloropsis australis*, and *Nannochloropsis limnetica*. Examples of algae belonging to the genus *Microchloropsis* include *Microchloropsis salina* and *Microchloropsis gaditana*. An example of algae belonging to the genus *Pseudochoricystis* includes *Pseudochoricystis ellipsoidea*. An example of algae belonging to the genus *Phaeodactylum* includes *Phaeodactylum tricornutum*. An example of algae belonging to the genus *Ostreococcus* includes *Ostreococcus tauri*. An example of algae belonging to the genus *Cyanidioschyzon* includes *Cyanidioschyzon merolae*. An example of algae belonging to the genus *Klebsormidium* includes *Klebsormidium flaccidum*. An example of algae belonging to the genus *Chara* includes *Chara fragilis*. An example of algae belonging to the genus *Coleochaete* includes *Coleochaete scutata*. An example of algae belonging to the genus *Chlorella* includes *Chlorella vulgaris*.

An operation of introducing gene mutation into SPX gene, an operation of introducing the resultant into a microorganism, and the like can be performed in accordance with ordinary methods.

Culture of a gene knockout strain (microorganism) produced by the above-described method and a method described in the examples below can be performed in a similar manner as usual culture of a microorganism used except that the culture is performed under phosphorus deficient conditions at the time of TAG accumulation. For example, if an alga belonging to the genus *Nannochloropsis* is to be cultured as the microorganism, F2N medium or the like can be used as the medium, a culture temperature can be about 20 to 25° C., and light intensity employed for the culture can be 10 to 40 µE/m$^2$/sec. If an alga belonging to the genus *Chlamydomonas* is to be cultured, TAP medium or the like can be used as the medium, a culture temperature can be about 23 to 25° C., and light intensity employed for the culture can be 10 to 40 µE/m$^2$/sec.

If TAG is to be accumulated in the microorganism obtained in this manner, culture is performed under phosphorus deficient conditions. The culture under the phosphorus deficient conditions can be performed by using a medium obtained by removing a phosphorus component (such as K$_2$HPO$_4$, or KH$_2$PO$_4$) from the medium used for the growth, or reducing it to 3 µM or less. Usually, a sufficient amount of TAG is accumulated in a cell through the culture for about 8 to 13 days.

Besides, in using an alga capable of high density culture, such as an alga belonging to the genus *Nannochloropsis*, TAG can be accumulated, without transferring to a medium excluding a phosphorus component or the like, through culture under high density conditions for a prescribed period of time in the medium used for the growth. This is probably because a long-term culture naturally leads to nutrient salt deficient conditions. In the high density culture, a sufficient amount of TAG is usually accumulated in a cell through the culture for about 7 to 20 days. Here, the term "high density culture" usually refers to culture performed at a cell density of 1×10$^8$ cells/ml or more.

Collection of TAG from the cell in which TAG has been accumulated can be performed by an ordinary method.

EXAMPLES

Now, the present disclosure will be described in detail with reference to the examples. It is noted that the following examples are merely illustrative, and do not intend to limit the present disclosure.

Example 1

(Production of Gene Knockout Strain)

Figure 3:
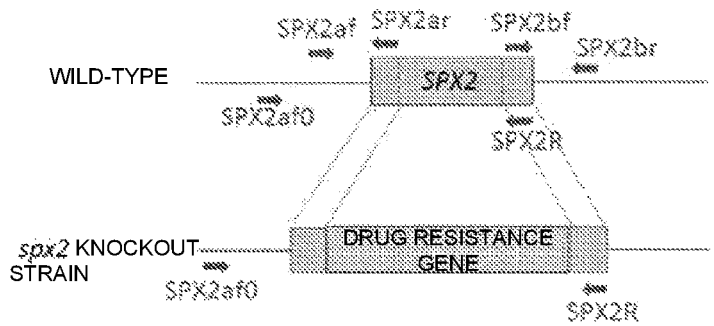
FIG. 3 is a diagram for explaining a method for producing an SPX2 gene knockout strain (spx2) according to the present disclosure.
Figure 3:
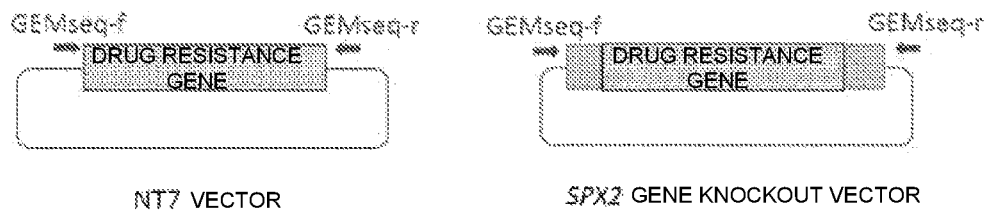

As illustrated in FIG. 3, an SPX2 gene knockout strain resulting from introduction of gene mutation into SPX2 gene was produced by replacing a part of SPX2 gene with a drug resistance gene (SEQ ID NO: 9).

Specifically, as illustrated in FIG. 3(*a*), a genomic DNA of *Nannochloropsis oceanica* NIES-2145 strain was used as a template of a microorganism to perform a PCR reaction using primers SPX2af (SEQ ID NO: 3) and SPX2ar (SEQ ID NO: 4) having nucleotide sequences respectively homologous to an upstream region of ORF (portion translated into a protein) of SPX2 gene and the ORF region of SPX2 gene, and having a recognition sequence for KpnI restriction enzyme added.

A DNA fragment amplified by the PCR reaction was subjected to an enzymatic treatment with KpnI restriction enzyme to insert a sequence of a first half portion of SPX2 gene (positions 541-1544 of SEQ ID NO: 13) into a KpnI restriction enzyme site GGTACC present immediately before a drug resistance gene in an NT7 vector having the drug resistance gene (Kilian et al., 2011: Proc. Natl. Acad. Sci. U.S.A. 108, 21265-21269. doi: 10.1073/pnas. 1105861108, Iwai et al., 2015 Front. Microbiol. 6: 912. doi: 10.3389/fmicb. 2015.00912) (SEQ ID NO: 10).

Subsequently, a second half portion (positions 2913-4057 of SEQ ID NO: 13) of SPX2 gene (specifically, a portion obtained by a PCR reaction using a genomic DNA as a template and using primers SPX2bf (SEQ ID NO: 5) and SPX2br (SEQ ID NO: 6)) was inserted into a PstI restriction enzyme site CAGCTG present immediately after the drug resistance gene in a plasmid obtained as described above.

As illustrated in FIG. 3(*b*), a PCR reaction was performed by using the plasmid (knockout vector for SPX2 gene) as a template and using primers GEMseq-f (SEQ ID NO: 7) and GEMseq-r (SEQ ID NO: 8) to introduce the resultant DNA fragment into *Nannochloropsis*. One produced through these operations is designated as an SPX2 gene knockout strain (also referred to simply as "spx2").

Sequences of the primers used for producing the SPX2 gene knockout strain (spx2) are as follows:

|  |  |
|---|---|
| SPX2af | (SEQ ID No. 3)<br>aaaggtaccGCCACTCATAAAGAGCATAA |
| SPX2ar | (SEQ ID No. 4)<br>aaaggtaccAAAAATTGCTCGCCCACCTC |
| SPX2bf | (SEQ ID No. 5)<br>AAAACGACTGCGCTGTCTGC |
| SPX2br | (SEQ ID No. 6)<br>TGAGTCCCTTGCTGGCTGCT |
| GEMseq-f | (SEQ ID No. 7)<br>GTTTTCCCAGTCACGAC |
| GEMseq-r | (SEQ ID No. 8)<br>CAGGAAACAGCTATGAC |

The specific procedure of gene transfection into *Nannochloropsis* are as follows (Vieler et al., 2012. PLoS Genet. 8: e1003064. doi: 10.1371/journal. pgen. 1003064):

1. Culture was performed under basic culture conditions at a cell density of 2.5×10$^6$ cells/ml.

2. Cells on day 3 of culture were collected in a clean bench, and centrifuged at 4900 rpm for 5 minutes at 4° C. using HIMAC™ CR20GIII centrifuge (HIKOKI Co., Ltd. manufacturer).

3. After the centrifugation, a supernatant was discarded, 50 ml of 375 mM sorbitol was added thereto, and the resultant was centrifuged at 4900 rpm for 7 minutes at 4° C. to wash the cells.

4. This washing operation was repeated twice.

5. After the washing, a supernatant was discarded, a small amount of 375 mM sorbitol was added thereto for suspension, and the number of cells was counted.

6. In a clean bench, 100 µL of *Nannochloropsis*, 3 µg of DNA, and 3 µg of salmon sperm DNA were added to a 0.2 cm GENE PULSER® cuvette.

7. The resultant cells were set in GENE PULSER XCELL™ electroporation system of BIO-RAD Laboratories for electroporation to introduce the gene. Values set were a voltage of 2200 V, a capacitance of 50 μF, a resistance of 600Ω, and a cuvette length of 2 mm.

8. After the gene transfection, in a clean bench, 5 ml of F2N medium (PNAS, 2011, vol. 108 (no. 52) 21265-21269) was put in a 15 ml tube, and the cells resulting from the gene transfection were added thereto.

9. Thereafter, recovery culture was performed with shaking under basic culture conditions for 2 days. In this recovery culture, the tube was covered with a paper towel to perform the culture with light rather shielded.

10. In a clean bench, a supernatant was discarded, 10 ml of 0.4% Top agar was added thereto for suspension, and the resultant cells were seeded in precedently prepared ZEOCIN® phleomycin D1 F2N agar media in a total number of 4, with 2 media for each DNA.

11. Thereafter, the resultant plates were sealed with a surgical tape, and culture was performed in an incubator set to 25° C. and 30 μmol photons/m$^2$s.

(Production of Control Strain)

On the other hand, a control strain was produced as follows: As illustrated in FIG. 3(b), a PCR reaction was performed, with an unmodified NT7 vector used as a template, by using primers GEMseq-f and GEMseq-r in the same manner as described above, and the thus obtained DNA fragment was introduced into *Nannochloropsis*. Through this operation, a control strain (also referred to simply as "NT7") was produced.

(Confirmation of Gene Knockout)

Next, it was confirmed by colony PCR that gene knockout of SPX2 gene had normally occurred.

Specifically, in the procedure of the gene transfection into *Nannochloropsis* described above, a colony produced in Zeocin F2N agar medium was poked, and the resultant was cultured in a 96-well plate containing Zeocin F2N medium. A culture fluid was taken out, and cells were collected by centrifugation, suspended in 100 μl of TE buffer, and heat treated at 95° C. for 5 minutes. The thus obtained liquid was used to perform a PCR reaction using primers SPX2af0 (SEQ ID NO: 11) and SPX2R (SEQ ID NO: 12).

On the other hand, as a control, a PCR reaction was performed in the same manner as described above using a genome extract of a wild-type strain.

Figure 4:
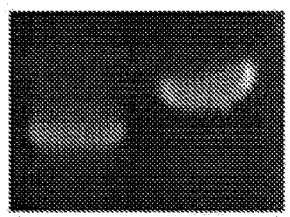
FIG. 4 illustrates electrophoretic patterns for confirming gene knockout of the SPX2 gene knockout strain (spx2) of the present disclosure.
Figure 4:
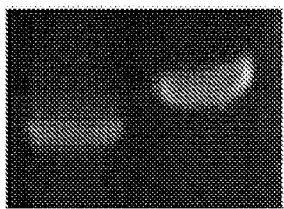

The thus obtained DNA fragment was subjected to electrophoresis in TAE agarose gel, and as a result, it was confirmed that a molecular size of the DNA fragment of the SPX2 gene knockout strain (spx2) and a size of wild-type SPX2 gene are different. Results are illustrated in FIG. 4.

Sequences of the primers used for confirming the gene knockout are as follows:

SPX2af0 atggctgaatgtgtacccgtgt (SEQ ID No. 11)

SPX2R CTAGACCTCATCCTGCTTCA (SEQ ID No. 12)

Example 2

(Analysis 1 of Cell Growth Ability and TAG Accumulation Ability of SPX2 Gene Knockout Strain (spx2) and Control Strain (NT7) in Various Media)

In each of various media (F2N medium, —P medium and —N medium), 3 samples of the control strain (NT7) and 3 samples of the SPX2 gene knockout strain (spx2) (18 samples in total) were cultured to perform the following measurements.

(1) Various Media

The compositions of the various media are as follows:

(1-1) F2N Medium

F2N medium (also referred to simply as "F2N") is a control medium (usual medium), and was prepared as follows. 0.1 ml of NaNO$_3$ (75 mg/ml), 0.1 ml of NaH$_2$PO$_4$·2H$_2$O (30 mg/ml), 0.1 ml of Na$_2$SiO$_3$·9H$_2$O (10 mg/ml), 0.5 ml of F/2 metals, 1 ml of NH$_4$Cl (500 mM), 1 ml of tris-HCl (pH 7.6) (1 M), and 3.6 g of Daigo Artificial Seawater SP [FUJIFILM Wako Pure Chemical Corporation] were dissolved in ion exchanged water to prepare the medium in an amount of 100 ml. Here, F/2 metals were prepared by dissolving, in ion exchanged water, 440 mg of Na$_2$EDTA·2H$_2$O, 316 mg of FeCl$_3$·6H$_2$O, 1.2 mg of CoSO$_4$·7H$_2$O, 2.1 mg of ZnSO$_4$·7H$_2$O, 18 mg of MnCl$_2$·4H$_2$O, 0.7 mg of CuSO$_4$·5H$_2$O, and 0.7 mg of Na$_2$MoO$_4$·2H$_2$O to obtain an amount of 100 ml. Besides, the thus prepared F2N medium and F/2 metals were stored at 4° C.

(1-2) —P Medium

—P medium (also referred to simply as "—P") is a phosphorus deficient medium, and is obtained by removing NaH$_2$PO$_4$·2H$_2$O from F2N medium.

(1-3) —N Medium

—N medium (also referred to simply as "—N") is a nitrogen deficient medium, and is obtained by removing NaNO$_3$ and NH$_4$Cl from F2N medium.

(2) Culture Conditions

A shaking incubator equipped with 3-color LED illumination (Nippon Medical & Chemical Instruments Co., Ltd., Low Temperature Incubator LP-200P, 3 in 1 LED lighting unit) was used to perform shaking culture of the SPX2 gene knockout strain (spx2) and the control strain (NT7) in 100 ml of each of the various media held in a 300 ml flask.

Specific culture conditions were a temperature of 25° C., a light intensity of 30% for all the colors (50 μmol photons/m$^2$s), a shaking rate of 100/min, an initial cell density of 2.5×10$^6$ cell/ml with CO$_2$ not allowed to pass. Before starting the culture, the following vitamins and drug were added. The composition of the vitamins and the drug is 5 μl of vitamin B12 (50 μg/ml), 5 μl of biotin (50 μg/ml), 50 μl of thiamine HCl (1 mg/ml), and 10 μl of Zeocin (20 mg/ml).

(3) Various Measurements

A cell density and a cellular chlorophyll content in each of the various media were measured every day, and this measurement was performed for 10 days. On the 10th day, a dry weight (biomass, dry matter) of the cells was measured, and sampling for TAG analysis was performed.

(3-1) Measurement of Cell Density

A bacteria counter (hemocytometer) was used to measure the number of cells with an optical microscope. Results are illustrated in FIG. 6(a).

(3-2) Measurement of Cellular Chlorophyll Content

A specific procedure for measuring a cellular chlorophyll content is as follows. Results are illustrated in FIGS. 6(b) and 6(c).

1. In a clean bench, a sample was transferred from the medium used for the culture and held in the 300 ml flask to a 1.5 ml tube.

2. The 1.5 ml tube was centrifuged at 7000 G for 10 minutes at 25° C.

3. After the centrifugation, a supernatant was removed, an appropriate amount of methanol was added to the 1.5 ml tube for suspension, and the 1.5 ml tube was set in a tube mixer for stirring for 5 minutes.

4. The 1.5 ml tube after the stirring was centrifuged at 10000 G for 5 minutes at 25° C.

5. After the centrifugation, a supernatant was collected, and absorbances at 650 nm and 665 nm were measured using a NANODROP® spectrophotometer.

6. Based on the measurement result, the chlorophyll content was determined in accordance with the following expression. It is noted that the following expression was employed because *Nannochloropsis* has merely chlorophyll a in the chloroplast.

Expression: "Chlorophyll Content" (µg Chl/ml)="Dilute Concentration"דOD665 (absorbance at 665 nm)"×13.4

7. Based on the experiment for determining the chlorophyll content and the experiment for measuring the cell density, the chlorophyll content in a single cell was derived.

(3-3) Measurement of Biomass (Dry Weight of Cell)

Figure 7:
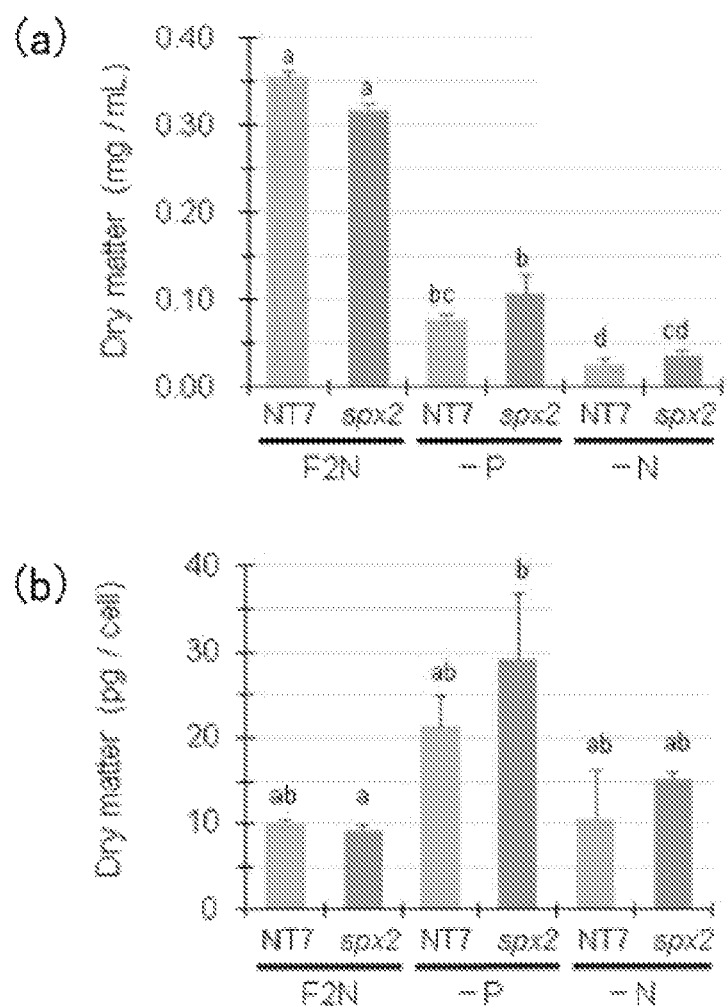
FIG. 7 is a diagram illustrating (a) a biomass (dry weight of cells) per unit medium, and (b) a biomass per cell obtained 10 days after starting culture of the SPX2 gene knockout strain (spx2) and the control strain (NT7) in FIG. 5.

A specific procedure for measuring biomass (dry matter, DM) is as follows. Results are illustrated in FIG. 7.

1. The weight of a 1.5 ml tube was measured with an electronic balance.

2. From the medium on day 10 counted from the next day of the day starting the culture, 40 ml of the culture fluid was taken out to be transferred to a 50 ml tube.

3. The 50 ml tube was centrifuged at 4670 G for 10 minutes at 25° C.

4. After the centrifugation, a supernatant was removed carefully not to remove cells.

5. $H_2O$ was added to the resultant precipitate for suspension, and the resultant was transferred to the 1.5 ml tube whose weight had been measured. The resultant was centrifuged at 7000 G for 10 minutes at 25° C.

6. A supernatant was removed without removing cells, and the resultant was put in a high temperature dryer to be dried at 105° C. for 5 hours with a cap removed.

7. The 1.5 ml tube was taken out of the high temperature dryer, and biomass was measured with an electronic balance.

8. Based on the experiments for measuring a cell density, biomass per a single cell was derived.

(3-4) Observation of Cell with Microscope

Figure 8:
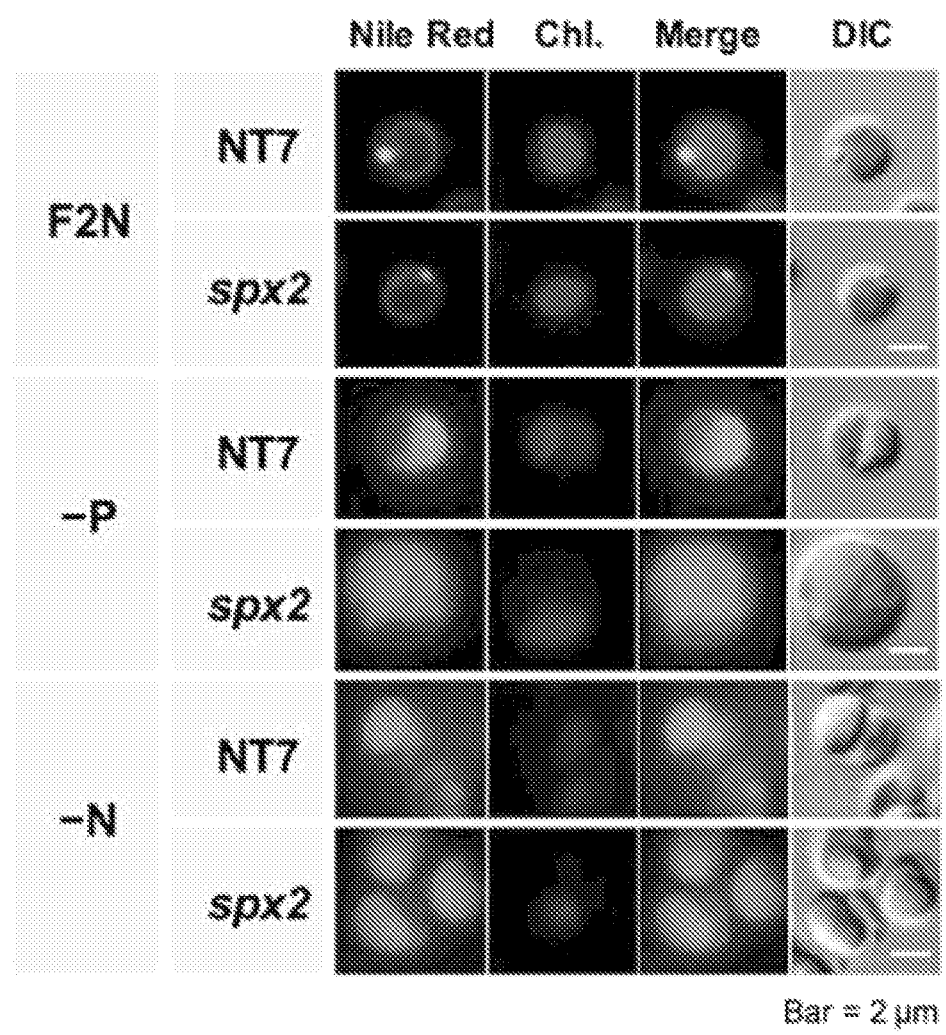
FIG. 8 illustrates photographs of stained cells of the SPX2 gene knockout strain (spx2) and the control strain (NT7) obtained 10 days after starting the culture in FIG. 5. In the drawing, Nile Red indicates fluorescence of stained TAG, Chl. indicates autofluorescence of a chloroplast, Merge indicates an image obtained by overlapping Nile Red and Chl., and DIC indicates a differential interference microscope image.

To 100 µl of a culture fluid, 100 µl of a fixative (50 mM PIPES, 4% paraformaldehyde) and 1 µl of 0.2 mg/ml Nile Red dye solution were added, and the resultant was allowed to stand still in the dark at 4° C. for 1 or more hours. Thereafter, the resultant was observed with AXIO IMAGER™r M2 microscope (CARL ZEISS manufacturer). Results are illustrated in FIG. 8.

(3-5) Quantitative Determination of TAG (Extraction of Lipid)

Figure 9:
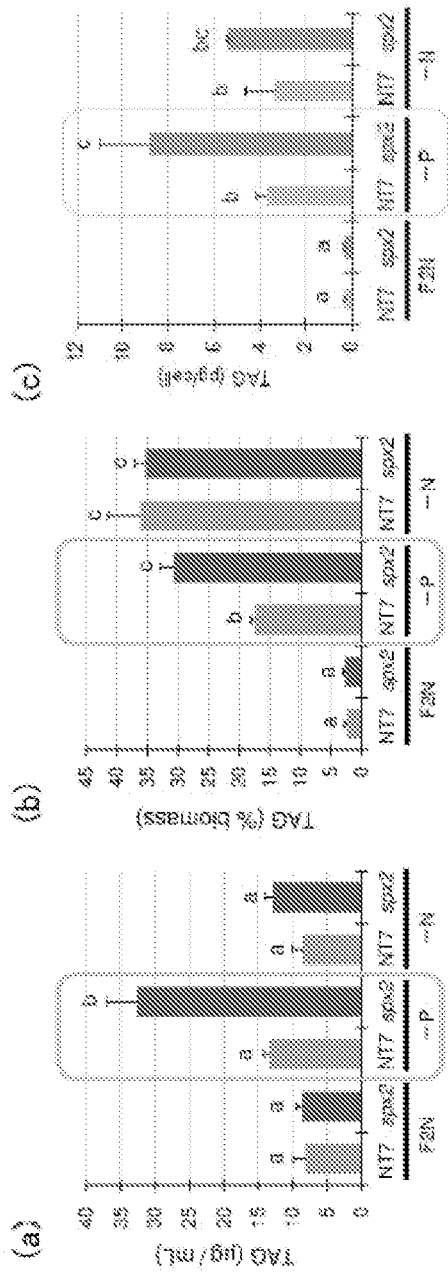
FIG. 9 is a diagram illustrating (a) an amount of TAG per unit medium, (b) an amount of TAG per unit biomass, and (c) an amount of TAG per cell obtained 10 days after starting the culture of the SPX2 gene knockout strain (spx2) and the control strain (NT7) in FIG. 5.

A lipid (TAG) was extracted from the cultured cells by the Bligh & Dyer method (Bligh, E. G. and Dyer, W. J. (1959) A rapid method of total lipid extraction and purification, Can. J. Biochem. Physiol. 37, 911-917, doi: 10.1139/059-099). A specific procedure for extracting the lipid was as follows. Results are illustrated in FIG. 9.

First, from a medium on day 10, 40 ml of the culture fluid was taken out and transferred to a 50 ml tube, and the 50 ml tube was centrifuged at 4670 G for 10 minutes at 25° C. for precipitating cultured cells. After the centrifugation, a supernatant was removed, and the precipitated cultured cells were rapidly frozen with liquid nitrogen, and stored at −80° C.

Subsequently, the frozen cells were thawed, and the cells held in the 50 ml tube were suspended in $H_2O$ in such a manner as to attain a total liquid amount of 0.8 ml, and the resultant was transferred to a glass test tube. To the glass test tube, 3 ml of a mixture of chloroform:methanol=1:2 was added, and the resultant was allowed to stand at room temperature for 1 hour with stirring every 10 minutes. Thereafter, 1 ml of $H_2O$ and 1 ml of chloroform were added to the glass test tube for suspension, and the resultant was centrifuged at 2000 rpm for 5 minutes using a swing rotor. After the centrifugation, an aqueous methanol layer (upper layer) was removed, and a chloroform layer (lower layer) was transferred to a new glass test tube. On the other hand, 1.5 ml of chloroform was added to the prior glass test tube for suspension. The prior test tube with the suspension and the new test tube to which the chloroform layer had been transferred were both centrifuged at 2000 rpm for 5 minutes using a swing rotor. After the centrifugation, the chloroform layer of the new test tube was transferred to another test tube whose weight had been measured. The chloroform layer obtained in the prior test tube was collected, centrifuged at 2000 rpm for 5 minutes using a swing rotor for collecting a chloroform layer, which was mixed with the aforementioned chloroform extract to obtain a lipid extract. The lipid extract was dried with a vacuum concentrator, and the resultant was dissolved in chloroform to a concentration of 10 mg/ml, and then stored at −20° C. When the amount of a sample was less than 1 mg, it was dissolved in 150 µl of chloroform.

(Lipid Analysis)

Figure 10:
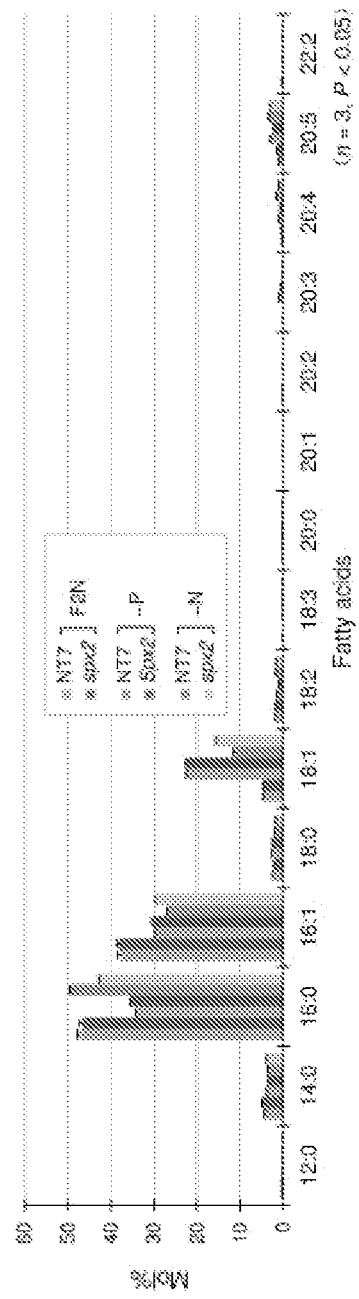
FIG. 10 is a diagram illustrating a fatty acid composition of TAG obtained 10 days after starting the culture of the SPX2 gene knockout strain (spx2) and the control strain (NT7) in FIG. 5. Respective bar graphs indicate, successively in a left-to-right direction, the control strain (NT7) cultured in F2N, the SPX2 gene knockout strain (spx2) cultured in F2N, the control strain (NT7) cultured in —P, the SPX2 gene knockout strain (spx2) cultured in —P, the control strain (NT7) cultured in —N, and the SPX2 gene knockout strain (spx2) cultured in —N. Besides, the abscissa in the drawing indicates "Carbon Number: Number of Unsaturated Bonds" of each fatty acid.

One (1) mg of all lipids (or a half amount of a sample if the amount of all the lipids in the sample was less than 1 mg) was spotted on a thin layer silica plate (silica gel 60 of Merck) to be developed for 40 minutes with a developing liquid of hexane: diethyl ether: acetic acid=40:20:1. TAG was detected under UV irradiation by using 0.01% primulin. A portion of the silica having TAG thereon was scraped off and transferred to a test tube. To the test tube, 2.5 ml of a methylation solution (5% hydrochloric acid/methanol) was added, and the resultant was heated at 85° C. for 2.5 hours. After cooling to ordinary temperature, 2.5 ml of hexane was added to the resultant test tube for suspension, the resultant was allowed to stand still, and an upper hexane layer was collected. Fatty acid having been methyl-esterified and collected in the hexane layer was dried, and the resultant was dissolved in a small amount of hexane to obtain a gas chromatography sample. The gas chromatography was analyzed with ULBON HR-SS-10 25 m, having an inner diameter of 0.25 mm and a film thickness of 0.25 µm (Shinwa Chemical Industries Ltd., Japan) set in GC-2014 (autosampler AOC-20i) manufactured by Shimadzu Corporation. Helium was used as a carrier gas. Results of lipid analysis thus performed are illustrated in FIG. 10.

(3-6) Determination of Amount of Polyphosphate

A specific procedure for measuring the amount of polyphosphate is as follows. Cells were collected from 20 ml of a culture fluid of F2N media on day 4 and day 7, and the cells were washed with pure water. After washing, the number of cells was measured, $5 \times 10^7$ cells or $1 \times 10^8$ cells were fractionated, suspended in 100 µl of a 5% sodium hypochlorite solution, and frozen with liquid nitrogen. With special beads put in a tube, the resultant was disrupted at 30 Hz for 10 minutes with Tissue Lyser (Qiagen K.K.). The disrupted lysate was transferred to a new tube, and 0.9 ml of a sodium hypochlorite solution was added thereto, followed by centrifugation at 14,000 G for 5 minutes. After the centrifugation, a supernatant was removed, the resultant precipitate in the tube was suspended in 1 ml of a sodium hypochlorite solution, followed by centrifugation at 14,000 G for 5 minutes. After the centrifugation, a supernatant was removed, the resultant precipitate in the tube was suspended in 100 µl of pure water, and the resultant was mixed for 5 minutes at room temperature with a tube mixer, followed by centrifugation at 14,000 G for 5 minutes. After the centrifugation, a supernatant was transferred to a new tube, the resultant precipitate in the prior tube was suspended in 100 µl of pure water, and the resultant was mixed for 5 minutes with a tube mixer, followed by centrifugation at 14,000 G for 5 minutes. After the centrifugation, the resultant supernatant was additionally added to the new tube, and the resultant was mixed to be dispensed into two tubes. To each of the dispensed two tubes, 0.9 ml of 100% ethanol was added and mixed, followed by centrifugation at 14,000 G for 10 minutes. After the centrifugation, a supernatant was discarded, the precipitate in each of the two tubes was suspended in 25 μl of pure water, and the resultants were collected in one tube again. Ultimately, 100 μl of 4% potassium peroxodisulfate was added to the tube, and the resultant was heated and compressed at 121° C. for 30 minutes in an autoclave. In the thus obtained solution, the phosphate amount was determined using Malachite Green Phosphate Assay Kit (BioChain). Results are illustrated in FIG. 11.

(3-7) Determination of Cell Size

Figure 12:
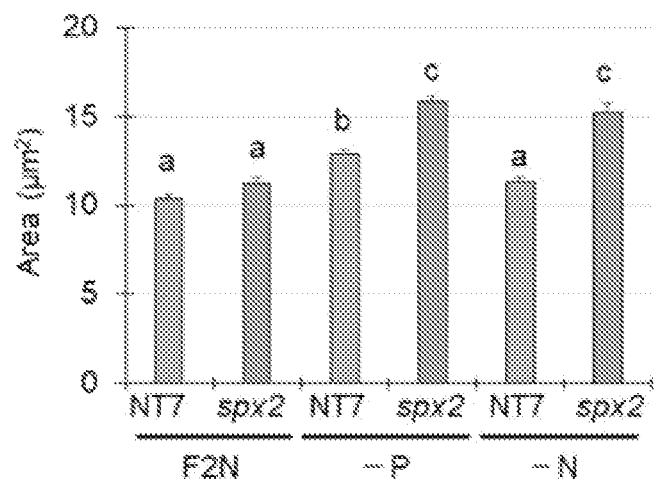
FIG. 12 is a diagram illustrating a size of each cell measured and determined based on a microscope photograph of each sample used in FIG. 8.

Microscopic images of samples used in "(3-4) Observation of Cells with Microscope" were taken. Subsequently, a cell area in each image thus taken was determined using image analysis software, Image J (https://imagej.nih.gov/ij/). Results are illustrated in FIG. 12.

(Results of Experiments)

(1) Cell Growth Ability and Cellular Chlorophyll Content

Figure 5:
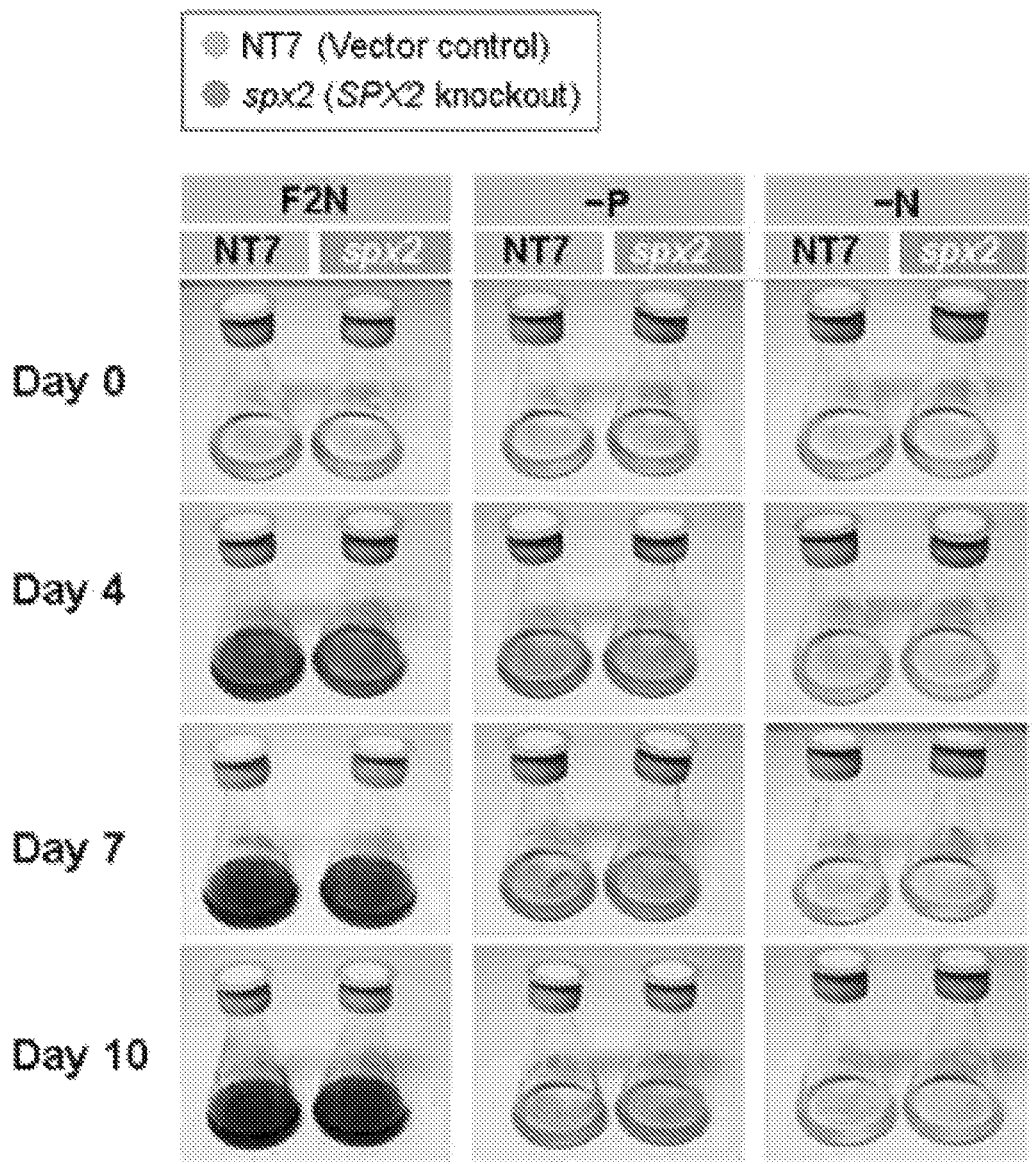
FIG. 5 illustrates photographs showing states of culture fluids obtained 0 day, 4 days, 7 days and 10 days after starting culture of a control strain (NT7) and the SPX2 gene knockout strain (spx2) in various media. In the drawing, F2N indicates a state cultured in a control medium, —P indicates a state cultured in a phosphorus deficient medium, and —N indicates a state cultured in a nitrogen deficient medium.
Figure 6:
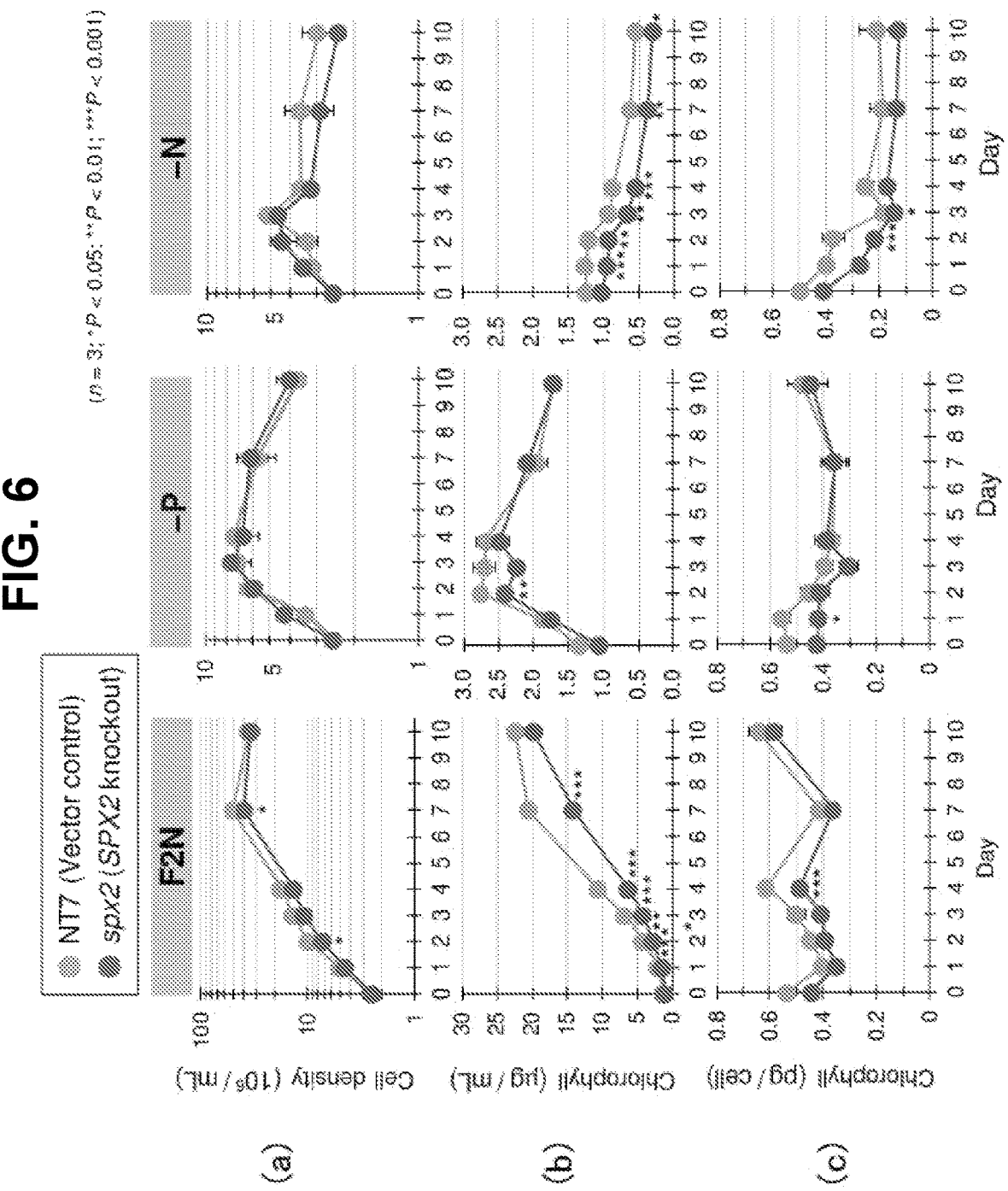
FIG. 6 illustrates (a) a cell density, (b) a chlorophyll content per unit medium, and (c) change of a chlorophyll content per cell occurring in a culture period obtained in FIG. 5.

As illustrated in FIG. 5 and FIG. 6, it was found that the SPX2 gene knockout strain (spx2) had a higher cell growth ability and a higher cellular chlorophyll content under phosphorus deficiency (—P) than under nitrogen deficiency (—N) in the same manner as the control strain (NT7). Besides, it was found that the SPX2 gene knockout strain (spx2) is slightly lowered in the growth ability under usual conditions (F2N) as compared with the control strain (NT7), but exhibits a growth rate equivalent to that of the control strain (NT7) under nitrogen deficiency (—N) and under phosphorus deficiency (—P). The chlorophyll content per unit culture fluid was reduced in the SPX2 gene knockout strain (spx2) under usual conditions (F2N) and under nitrogen deficiency (—N) as compared with the control strain (NT7), but was equivalent to that of the control strain (NT7) under phosphorus deficiency (—P).

(2) Biomass (Dry Weight of Cell)

As illustrated in FIG. 7, it was found that the SPX2 gene knockout strain (spx2) has higher biomass per cell under phosphorus deficiency (—P) than under usual conditions (F2N).

(3) Oil Droplet Accumulated in Cell

As illustrated in FIG. 8, it was found that in the SPX2 gene knockout strain (spx2), an oil droplet accumulated in a cell develops under phosphorus deficiency (—P).

(4) TAG Accumulation Ability

As illustrated in FIG. 9, it was found that the SPX2 gene knockout strain (spx2) has a significantly high amount of accumulated TAG under phosphorus deficiency (—P) with respect to any one of per unit medium, per unit biomass, and per cell as compared with the control strain (NT7), and thus TAG is accumulated in cells.

(5) Fatty Acid Composition of TAG

As illustrated in FIG. 10, there was no change in the fatty acid composition of TAG between the SPX2 gene knockout strain (spx2) and the control strain (NT7) in any of experimental plots. Under phosphorus deficiency (—P), in both of the strains, reduction of C16:0 (carbon number of 16, no unsaturated bond) and increase of C18:1 (carbon number of 18, 1 unsaturated bond) were significant as compared with the cases in the other media.

(6) Accumulation Ability of Polyphosphate

As illustrated in FIG. 11, it was found that the amount of polyphosphate per cell is reduced in the SPX2 gene knockout strain (spx2) under usual conditions (F2N) as compared with that in the control strain (NT7).

(7) Cell Size

As illustrated in FIG. 12, it was found that under nitrogen deficiency (—N) or under phosphorus deficiency (—P), the SPX2 gene knockout strain (spx2) had a larger cell than the control strain (NT7). Under usual conditions (F2N), however, the cell sizes were similar therebetween.

Example 3

(Analysis 2 of TAG Accumulation Ability of SPX2 Gene Knockout Strain (spx2) and Control Strain (NT7) in Various Media)

In each of various media different from those of Example 2 (P250 medium, P15 medium, and P0 medium) and under the following different culture conditions, 3 samples of the control strain (NT7) and 3 samples of the SPX2 gene knockout strain (spx2) (18 samples in total) were cultured to perform the following measurements. Specifically, in Example 3, cells were cultured, as compared with the culture conditions of Example 2, with the concentration of nutrient salts in each medium increased, with the light intensity increased, and with carbon dioxide added, under high density culture condition where the initial cell density was increased by 40 times.

(1) Various Media

Compositions of the various media are as follows:

(1-1) P250 Medium

P250 medium (also referred to simply as "P250") is a control medium (usual medium), and was prepared as follows. 2.5 g of $KNO_3$, 250 mg of $Na_2HPO_4$, 75 mg of Fe-EDTA, 5 ml of an A5 stock solution, and 35 g of Daigo Artificial Seawater SP [FUJIFILM Wako Pure Chemical Corporation] were dissolved in ion exchanged water to prepare the medium in an amount of 1 L. Here, the A5 stock solution was prepared by dissolving, in ion exchanged water, 222 mg of $ZnSO_4 \cdot 7H_2O$, 79 mg of $CuSO_4 \cdot 5H_2O$, 15 mg of $MoO_3$, 2.86 g of $H_3BO_3$, and 1.81 g of $MnCl_2 \cdot 4H_2O$ to obtain an amount of 1 L. Besides, the thus prepared P250 media and A5 stock solution were stored at 4° C.

(1-2) P15 Medium

P15 medium (also referred to simply as "P15") is a medium having a low phosphorus concentration obtained by changing the concentration of $Na_2HPO_4$ of P250 medium from 250 mg/L to 15 mg/L.

(1-3) P0 Medium

P0 medium (also referred to simply as "P0") is a phosphorus deficient medium obtained by removing $Na_2HPO_4$ from P250 medium.

(2) Culture Conditions

A biotron (Nippon Medical & Chemical Instruments Co., Ltd., Model LH-241S special) was used to perform aerobic culture of the SPX2 gene knockout strain (spx2) and the control strain (NT7) in 50 ml of each of the various media held in a 100 ml test tube.

Specific culture conditions were a temperature of 25° C., a light intensity of white light (250 μmol photons/m s), an initial cell density of $1 \times 10^8$ cells/ml, and an air flow rate of 15 ml/min (2% $CO_2$). Before starting the culture, the following vitamin mixture and drug were added. The composition of the vitamin mixture and the drug is 2 ml of a mixture of vitamin B12 (60 μg/L), biotin (30 μg/L), and thiamine HCl (6 mg/L), and 100 μl of Zeocin (20 mg/ml).

(3) Quantitative Determination of TAG

Figure 13:
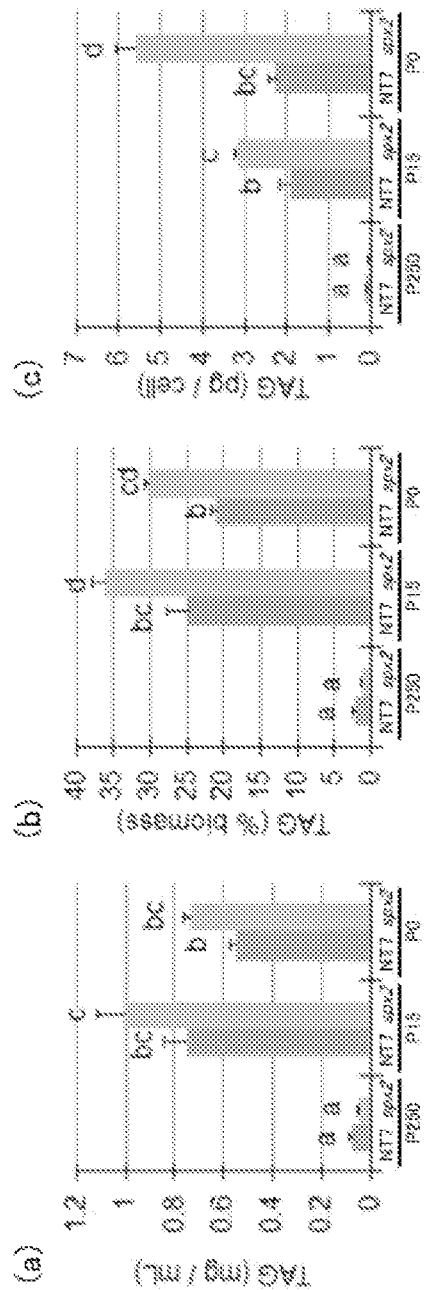
FIG. 13 is a diagram corresponding to FIG. 9 obtained 7 days after starting culture of the SPX2 gene knockout strain (spx2) and the control strain (NT7) in various media different from those used in FIG. 9. In the drawing, P250 indicates a state cultured in a control medium, P15 indicates a state cultured in a medium having a low phosphorus concentration, and P0 indicates a state cultured in a phosphorus deficient medium.

On the 7th day, a cell density and a dry weight (biomass, dry matter) of cells in each of the various media were measured, and sampling for TAG analysis was performed. Thereafter, TAG was quantitatively determined in the same manner as in the procedure described in "(3-5) Quantitative Determination of TAG" of Example 2 except for the number of culture days and the amount of a culture fluid, more specifically, except that 10 ml of a culture fluid was taken out from each medium on day 7 counted from the next day of the day starting the culture, and transferred to a 50 ml tube. Results are illustrated in FIG. 13. To make a quantitative determination of TAG, the measurement of the cell density was performed in the same manner as in the method described in "(3-1) Measurement of Cell Density" of Example 2. Besides, the measurement of the dry weight of cells was performed in the same manner as in the procedure described in "(3-3) Measurement of Biomass (dry weight of cell)" of Example 2 except for the number of culture days and the amount of a culture fluid, more specifically, except that 10 ml of a culture fluid was taken out from each medium on day 7 counted from the next day of the day starting the culture, and transferred to a 50 ml tube.

(Experimental Results)

TAG Accumulation Ability

As illustrated in FIG. 13, it was found that the SPX2 gene knockout strain (spx2) has a significantly high amount of accumulated TAG under high density culture conditions with respect to any one of per unit biomass and per cell not only under phosphorus deficiency (P0) but also under low phosphorus concentration conditions (P15) in which a small amount of phosphate was added to the medium as compared with the control strain (NT7), and thus TAG is accumulated in cells.

(Effects)

On the basis of the aforementioned results, the SPX2 gene knockout strain (spx2) of the present disclosure can provide the following effects:

(1) The SPX2 gene knockout strain (spx2) of the present disclosure is suitable for sustainable biomass production using a microorganism because chloroplast function thereof is comparatively retained and biomass per cell is high under phosphorus deficiency.

(2) The SPX2 gene knockout strain (spx2) of the present disclosure is a microorganism capable of highly accumulating TAG because it can accumulate TAG superiorly to the control strain (NT7) under phosphorus deficiency. Besides, the method for producing TAG using the SPX2 gene knockout strain (spx2) of the present disclosure is an effective method for highly accumulating TAG in a microorganism.

(3) In the SPX2 gene knockout strain (spx2) of the present disclosure, fatty acid compositions of accumulated fats and oils have a distribution mainly having a carbon number of 16, and hence it is suitable for production of a fuel equivalent to light oil. Besides, depending on purification conditions and purification method, a liquid fuel such as a fuel equivalent to gasoline can be produced.

In this manner, the SPX2 gene knockout strain (spx2) of *Nannochloropsis*, that is, an example of the microorganism of the present disclosure, accumulates TAG at a significantly high level under phosphorus deficiency as compared with the control strain (NT7). This is probably for the following reason: Since SPX2 gene is presumed to encode a protein having polyphosphate synthesis activity (see FIG. 11), polyphosphate synthesis is inhibited by knockout of SPX2 gene. Thus, signal transduction for phosphate deficiency response becomes more active, and hence induction of secondary response is amplified, which possibly accelerates TAG accumulation.

On the other hand, as functions of VTC4 of yeast, vacuole fusion, microautophagy, and maintenance of stability of vacuolar proton ATPase are known in addition to the accumulation of polyphosphate. Accordingly, the following can be presumed: Knockout of the SPX2 gene inhibits vacuole fusion and microautophagy, and hence a recycling mechanism of phosphate in cells does not normally work, which may possibly more excessively cause phosphate deficiency response.

INDUSTRIAL APPLICABILITY

The present disclosure is applicable in various industrial fields related to TAG production.

---

The invention claimed is:

1. An alga belonging to the genus *Nannochloropsis* having at least one SPX gene encoding an SPX protein responsive to phosphorus deficiency, characterized in that a function of the SPX protein is decreased or lost by introducing a gene mutation into the SPX gene, the SPX gene encodes SEQ ID NO: 2, and the gene mutation deletes at least one amino acid residue selected from K250 (lysine at position 250 in SEQ ID NO: 2), R313 (arginine at position 313 in SEQ ID NO: 2), R315 (arginine at position 315 in SEQ ID NO: 2), K330 (lysine at position 330 in SEQ ID NO: 2), E466 (glutamic acid at position 466 in SEQ ID NO: 2), and K498 (lysine at position 498 in SEQ ID NO: 2).

2. A method for producing triacylglycerol, characterized by culturing the alga belonging to the genus *Nannochloropsis* according to claim 1 under phosphorus deficient conditions, causing triacylglycerol to be accumulated in cells of the alga, and collecting the accumulated triacylglycerol.

3. An alga belonging to the genus *Nannochloropsis* having at least one SPX gene encoding an SPX protein responsive to phosphorus deficiency, characterized in that a function of the SPX protein is decreased or lost by introducing a gene mutation into the SPX gene, the SPX gene encodes an amino acid sequence having an SPX domain and 60% or more homology with SEQ ID NO: 2, and the gene mutation deletes at least one amino acid residue corresponding to one selected from K250 (lysine at position 250 in SEQ ID NO: 2), R313 (arginine at position 313 in SEQ ID NO: 2), R315 (arginine at position 315 in SEQ ID NO: 2), K330 (lysine at position 330 in SEQ ID NO: 2), E466 (glutamic acid at position 466 in SEQ ID NO: 2), and K498 (lysine at position 498 in SEQ ID NO: 2).

4. The method of claim 2, characterized in that the alga belonging to the genus *Nannochloropsis* is cultured under high density conditions at cell density of $1\times10^8$ cells/ml or more.

5. A method for producing triacylglycerol, characterized by culturing the alga belonging to the genus *Nannochloropsis* according to claim 3 under phosphorus deficient conditions, causing triacylglycerol to be accumulated in cells of the alga, and collecting the accumulated triacylglycerol.

6. The method of claim 5, characterized in that the alga belonging to the genus *Nannochloropsis* is cultured under high density conditions at cell density of $1 \times 10^8$ cells/ml or more.

* * * * *